(12) United States Patent
Kumoyama

(10) Patent No.: US 8,366,760 B2
(45) Date of Patent: Feb. 5, 2013

(54) STENT DELIVERY SYSTEM

(75) Inventor: Kenichi Kumoyama, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 478 days.

(21) Appl. No.: 12/605,824

(22) Filed: Oct. 26, 2009

(65) Prior Publication Data

US 2010/0076541 A1 Mar. 25, 2010

Related U.S. Application Data

(63) Continuation of application No. PCT/JP2008/057877, filed on Apr. 23, 2008.

(30) Foreign Application Priority Data

Apr. 27, 2007 (JP) ................................. 2007-120195
Apr. 27, 2007 (JP) ................................. 2007-120196

(51) Int. Cl.
*A61F 2/06* (2006.01)

(52) U.S. Cl. ......................... 623/1.11; 623/1.2; 623/1.12

(58) Field of Classification Search ................. 623/1.12, 623/1.11, 1.1, 1.15, 1.2; 606/108, 200; 604/507, 604/264; 600/137
See application file for complete search history.

(56) References Cited

U.S. PATENT DOCUMENTS

| 5,534,007 | A | 7/1996 | St. Germain et al. |
| 5,683,451 | A | 11/1997 | Lenker et al. |
| 7,815,669 | B2 | 10/2010 | Matsuoka et al. |
| 2001/0034548 | A1 | 10/2001 | Vrba et al. |
| 2006/0259124 | A1* | 11/2006 | Matsuoka et al. ........... 623/1.12 |
| 2006/0282152 | A1* | 12/2006 | Beyerlein et al. ........... 623/1.11 |
| 2009/0204197 | A1 | 8/2009 | Dorn et al. |
| 2010/0331953 | A1 | 12/2010 | Matsuoka et al. |

FOREIGN PATENT DOCUMENTS

| JP | 8-38613 A | 2/1996 |
| JP | 8-173548 A | 7/1996 |

(Continued)

OTHER PUBLICATIONS

Supplementary European Search Report issued on Oct. 27, 2010 by the European Patent Office in the corresponding European patent application.
International Search Report (PCT/ISA/210) dated Jul. 15, 2008.
English translation of the International Preliminary Report on Patentability dated Nov. 24, 2009.

(Continued)

*Primary Examiner* — Gary Jackson
*Assistant Examiner* — Richard Louis
(74) *Attorney, Agent, or Firm* — Buchanan Ingersoll & Rooney PC

(57) ABSTRACT

A stent delivery system includes a distal-side tube having a guide wire lumen, a proximal-side tube, a fixing tube at which a proximal portion of the distal-side tube and a distal portion of the proximal-side tube are fixed and which has an opening communicating with the guide wire lumen, a stent accommodation tubular member which encloses a distal side of the distal-side tube and is slidable toward a proximal end of the distal-side tube, a stent accommodated inside the stent accommodation tubular member, and a pulling wire whose one end portion is fixed to the stent accommodation tubular member and which extends inside the proximal-side tube for moving the stent accommodation tubular member toward a proximal side by being pulled toward the proximal side.

20 Claims, 18 Drawing Sheets

FOREIGN PATENT DOCUMENTS

| | | | |
|---|---|---|---|
| JP | 11-505162 | A | 5/1999 |
| JP | 2002-534195 | A | 10/2002 |
| JP | 2003-521307 | A | 7/2003 |
| JP | 2005-103321 | A | 4/2005 |
| JP | 2006-305335 | A | 11/2006 |
| JP | 2007-97620 | A | 4/2007 |
| WO | WO 96/36298 | A1 | 11/1996 |
| WO | WO 01/54614 | A2 | 8/2001 |
| WO | WO 03/002019 | A2 | 1/2003 |
| WO | WO 03002019 | A2 * | 1/2003 |
| WO | WO 2006/133959 | A1 | 12/2006 |
| WO | WO 2006133959 | A1 * | 12/2006 |

OTHER PUBLICATIONS

Japanese Office Action issued Apr. 17, 2012 by the Japanese Patent Office in Japanese Patent Application No. 2007-120196, and partial English translation of Japanese Office Action , 3 pgs.

Japanese Office Action issued Jan. 17, 2012 by the Japanese Patent Office in Japanese Patent Application No. 2007-120195 and partial English language translation.

Japanese Office Action issued Jan. 24, 2012 by the Japanese Patent Office in Japanese Patent Application No. 2007-120196 and partial English language translation.

* cited by examiner

STENT DELIVERY SYSTEM

This application is a continuation of International Application No. PCT/JP2008/057877 filed on Apr. 23, 2008 and claiming priority to Japanese Patent Application No. 2007-120195 filed on Apr. 27, 2007 and Japanese Patent Application No. 2007-120196 filed on Apr. 27, 2007, the entire content of all of which is incorporated herein by reference.

TECHNICAL FIELD

The present invention relates to a stent delivery system for implanting a stent at a stenosed portion or a closed portion generated in internal organs such as a blood vessel, bile duct, trachea, esophagus, ureter, digestive tract, and the like.

BACKGROUND DISCUSSION

Stent delivery systems proposed heretofore are used to secure a lumen or a space in a body cavity by implanting the stent at the lumen, the stenosed portion or the closed portion of the body cavity in an internal organ such as a blood vessel, bile duct, trachea, esophagus, ureter, digestive tract, and the like.

Stents delivered by the stent delivery system are classified as balloon expandable stents and self-expandable stents, depending upon the function of the stent and the implantation method.

The balloon expandable stent itself has no expanding function. To implant the stent at a desired portion, after the stent is inserted into the desired portion, a balloon disposed in the stent is inflated to expand (plastic deformation) the stent by an expansive force of the balloon so that the stent is fixed, with the stent in close contact with the inner surface of the desired portion of the lumen.

It is necessary to perform the above-described operation of expanding the stent of this type in implanting it in the desired portion. The stent can be implanted in the desired portion by directly mounting it on the contracted balloon. Thus the balloon expandable stent does not have a problem in this respect.

On the other hand, the self-expandable stent itself has contracting and expanding functions. To implant the stent at a desired portion, after it is inserted into the desired portion in a contracted state, a stress applied for maintaining the contracted state is released. For example, the stent is accommodated in a sheath having a smaller diameter than the inner diameter of the desired portion of the lumen by contracting the stent. After the distal end of the sheath reaches the desired portion, the stent is pressed out of the sheath. Because the stent is released from the sheath, the applied stress is removed. The stent thus returns to the original configuration. Thereby the stent adheres to the inner surface of the desired portion.

Because the stent itself has an expandable force, it is unnecessary to perform the operation of expanding the stent of this type while implanting it in the desired portion, unlike the balloon expandable stent. Further there is no possibility that the diameter of the stent becomes smaller due to the pressure of the blood vessel and that a restenosis occurs again.

But compared with the balloon expandable stent, it is difficult to implant the self-expandable stent correctly at the desired portion for the reason described below. In the balloon expandable stent, after the stent is disposed at a desired stenosed portion, a liquid is injected into a balloon. Thus the stent does not move longitudinally when the stent is expanded. The delivery system of the self-expandable stent has a construction in which the stent is restrictedly accommodated between an inner tube and an outer tube, and a locking portion for restricting the movement of the stent is provided on the inner tube at a position located at the proximal side of the stent. By pulling the outer tube toward the proximal side of a system, the stent is released from the restricted state and expands itself. The stent is liable to move forward when it expands owing to loosening of the outer tube inside a body cavity or friction between the outer tube and the body cavity, between the outer tube and a catheter which introduces the outer tube or between the outer tube and a valve of a device called an introducer for introducing the delivery system into a patient's body.

Noting the above-described problem, the present applicant proposed the stent delivery system 1 disclosed in U.S. Patent Application Publication No. 2006/0259124. The stent delivery system 1 in this patent application publication includes a distal-side tube 2 having the guide wire lumen 21, a proximal-side tube 4 fixed to the proximal portion of the distal-side tube 2, a stent accommodation tubular member 5 which encloses the distal side of the distal-side tube 2 and is slidable in the proximal direction, a stent 3 accommodated inside the tubular member 5, and a pulling wire 6 for moving the tubular member 5 toward the proximal side. The distal-side tube 2 has a proximal-side opening 23, a stent-locking portion 22 for preventing the stent from moving toward the proximal side, and a operation part having the pulling wire winding mechanism and the wire winding amount prevention mechanism.

The stent delivery system 1 further includes an intermediate tube 7 which encloses the proximal side of the distal-side tube 2 and the proximal side of the stent accommodation tubular member 5 and is fixed to the proximal portion of the distal-side tube 2 and to the distal portion of the proximal-side tube 4 at the proximal portion thereof. The intermediate tube 7 encloses the proximal side of the distal-side tube 2 and the proximal side of the stent accommodation tubular member 5 without preventing the stent accommodation tubular member 5 from moving toward the proximal side. One end portion of the pulling wire 6 is fixed to the stent accommodation tubular member 5 inside the intermediate tube 7. The pulling wire 6 passes between the intermediate tube 7 and the distal-side tube 2, thus extending into the proximal-side tube 4.

Even though the self-expandable stent is used with the stent delivery system, the proximal-side opening is disposed not at the proximal end of an appliance, but at the proximal side of the distal-side tube. Therefore in a stent-implanting operation, an operation of exchanging the stent delivery system with other stent delivery systems can be relatively easily performed. By pulling the pulling wire toward the proximal side, the stent can be discharged. Therefore in a stent-discharging operation, the stent is moved in a very small amount. Further the stent delivery system has an advantage that in pulling a stent-binding member toward the proximal side, because the wire is not wound in an excessive amount, a catheter is prevented from being unnecessarily curved or damaged.

The stent delivery system disclosed in U.S. Patent Application Publication No. 2006/0259124 is sufficiently effective. With this stent delivery system, while inserting the stent into an organism, situations arise in which an insertion operation is performed by imparting a twist (torque) at the proximal side. The twist imparted at the proximal side may be transmitted to the stent accommodation tubular member through the distal portion of the intermediate tube. The twist imparted to the stent accommodation tubular member is also imparted to the stent accommodated therein with the inner surface thereof being pressed. The present inventors have found it is desirable not to impart the twist to the stent.

SUMMARY

According to one aspect, a stent delivery system includes a distal-side tube possessing a guide wire lumen through which a guide wire is adapted to extend, a proximal-side tube having an interior, a fixing tube fixed to a proximal portion of the distal-side tube and a distal portion of the proximal-side tube, a stent accommodation tubular member enclosing a distal side of the distal-side tube and slidable toward a proximal end of the distal-side tube, and a cylindrically-shaped stent accommodated inside the stent accommodation tubular member in a compressed condition and expandable outwardly when the stent is discharged from the stent accommodation tubular member so the stent returns to a configuration exhibited by the stent before being accommodated in the stent accommodation tubular member in the compressed condition. At least one pulling wire possesses one end portion fixed relative to the stent accommodation tubular member so that movement of the one end portion of the wire toward a proximal side of the stent accommodation tubular member causes movement of the stent accommodation tubular member toward the proximal side. The distal-side tube comprises a stent proximal portion-locking portion which contacts a proximal end of the stent accommodated inside the stent accommodation tubular member to prevent the stent from moving toward the proximal side, and a slide tube is disposed proximally of the proximal end of the stent accommodation tubular member. The slide tube is not fixed to the stent accommodation tubular member. The slide tube is movable toward the proximal side, together with the stent accommodation tubular member, when the pulling wire is pulled toward the proximal side so the slide tube either is received inside the fixing tube or receives the fixing tube.

In accordance with another aspect, a stent delivery system comprises a distal-side tube in which extends a guide wire lumen adapted to receive a guide wire to direct the stent delivery system to a desired site, with the guide wire lumen extending from the distal end of the distal-side tube to the proximal end of the distal-side tube, a proximal-side tube at least partially axially overlapping the distal-side tube, with the proximal-side tube possessing an interior, a fixing tube having a proximal portion fixed to the distal-side tube, with the fixing tube possessing an opening communicating with the guide wire lumen, and a stent accommodation tubular member surrounding a portion of the distal-side tube and possessing a proximal-most end located distally of a distal-most end of the proximal-side tube, with the stent accommodation tubular member surrounding a space. A stent is positioned in the space in a compressed condition and is expandable outwardly when the stent is discharged from the space in the stent accommodation tubular member. The device also comprises a pulling wire, connecting means for connecting the pulling wire and the stent accommodation tubular member so that the stent accommodation tubular member is moved in the proximal direction when a pulling force in the proximal direction is applied to the pulling wire, and a slide tube positioned axially between the stent accommodation tubular member and the fixing tube. The slide tube is not fixed to the stent accommodation tubular member. The slide tube is axially movable together with the stent accommodation tubular member and is axially movable relative to the fixing tube. The slide tube moves in the proximal direction relative to the fixing tube when the pulling wire is pulled in the proximal direction to cause axial overlap between the slide tube and the fixing tube that increases with continued movement of the slide tube in the proximal direction relative to the fixing tube.

DETAILED DESCRIPTION

Figure 1:
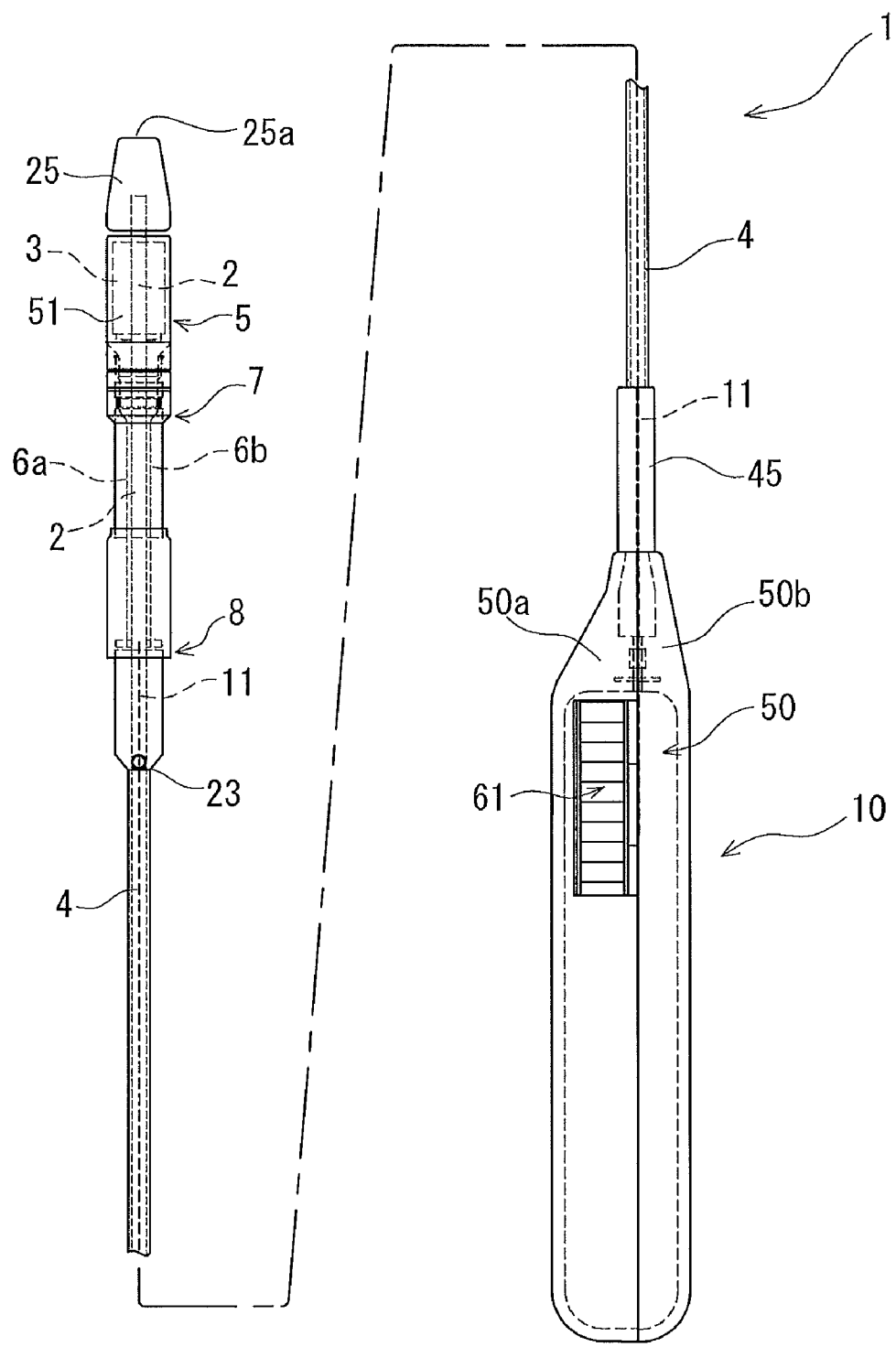
FIG. 1 is a partially exploded side view of a stent delivery system according to one embodiment disclosed here.

Set forth below is a description of various embodiments of stent delivery systems and/or alternative constructions which can be embodied in the various embodiments of the stent delivery system. Common features in the various embodiments are identified by common reference numerals.

Figure 2:
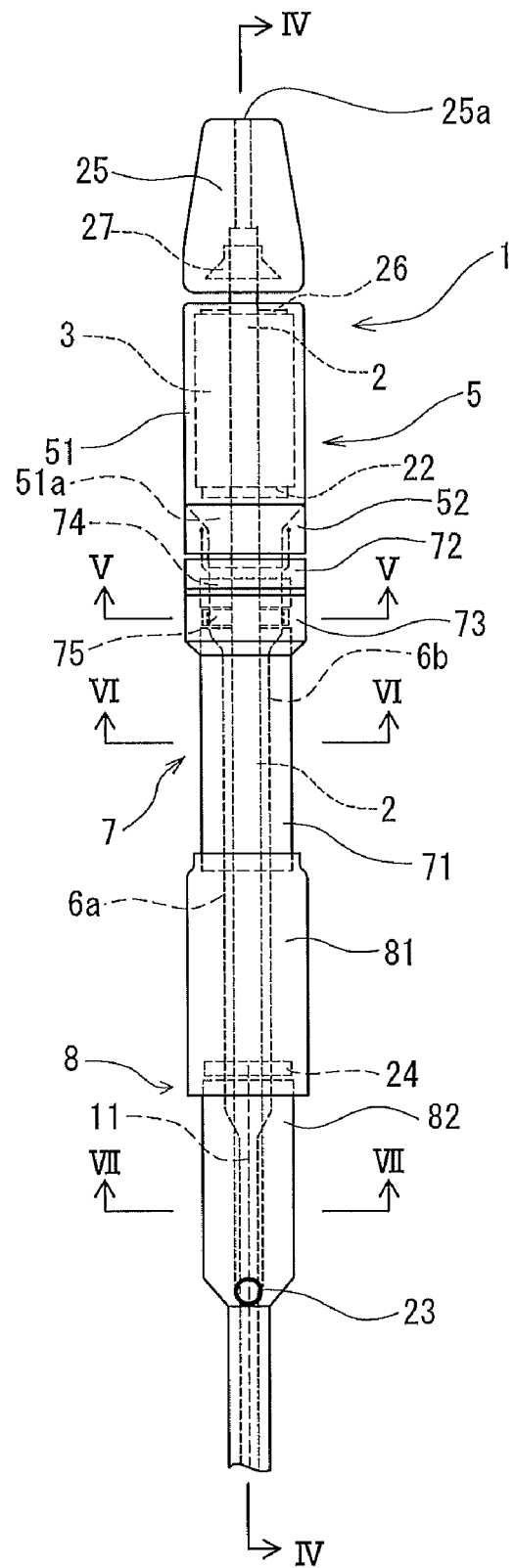
FIG. 2 is an enlarged side view of a distal portion of the stent delivery system shown in FIG. 1.

Referring initially to FIGS. 1 and 2, a stent delivery system 1 according to one disclosed embodiment disclosed here includes: a distal-side tube 2 having a guide wire lumen 21; a proximal-side tube 4 which axially overlaps the distal-side tube in the illustrated embodiment; a fixing tube 8 at which a proximal portion of the distal-side tube 2 and a distal portion of the proximal-side tube 4 are fixed together and which has an opening 23 communicating with the guide wire lumen 21; a stent accommodation tubular member 5 which encloses a distal part of the distal-side tube 2 and is slidable toward a proximal end of the distal-side tube 2; a stent 3 accommodated inside the stent accommodation tubular member 5; and a pulling wire 6 forming a moving means for moving the stent accommodation tubular member 5 toward a proximal side (in a proximal direction) by being pulled toward the proximal side. One end portion of the pulling wire 6 is fixed to the stent accommodation tubular member 5 and extends inside the proximal-side tube 4. In the illustrated embodiment, the pulling wire 6 is comprised of two wires 6a, 6b.

The stent delivery system of the present invention constitutes a body organ expansion appliance.

The distal-side tube 2 has a stent proximal portion-locking portion 22 shown in FIG. 2, disposed at a distal side of the distal-side tube 2. The stent proximal portion-locking portion 22 contacts a proximal end of the stent 3 accommodated inside the stent accommodation tubular member 5, thus preventing the stent 3 from moving toward the proximal side.

The stent 3 is formed approximately cylindrically and accommodated inside the stent accommodation tubular member 5. The stent 3 is axially compressed and expands outward when the stent 3 is discharged from the stent accommodation tubular member 5 so that the stent 3 returns to the configuration the stent had before the stent 3 is compressed.

The stent delivery system 1 includes a slide tube 7 disposed proximately to a proximal end of the stent accommodation tubular member 5. The fixing tube 8 is capable of accommodating the slide tube 7 from the proximal side thereof or the slide tube 7 can enclose the fixing tube 8 from the distal side thereof. By pulling the pulling wire 6, the slide tube 7 is movable toward the proximal side together with the stent accommodation tubular member 5. The slide tube 7 is not fixed to the stent accommodation tubular member 5. The slide tube 7 is positioned axially between the stent accommodation tubular member 5 and the fixing tube 8.

In the stent delivery system 1 disclosed here, it is preferable that the pulling wire 6 is fixed to the inner surface of the slide tube or to a member which is moved by being pulled by the pulling wire. It is especially preferable that the stent delivery system 1 of this embodiment includes a ring-shaped (annular) member 75 which is accommodated inside the slide tube 7 and moves together with the slide tube 7 and that the pulling wires 6a, 6b are fixed to the ring-shaped member 75.

In the stent delivery system 1 of this embodiment, the outer diameter of the proximal-side tube 4 is smaller than the outer diameter of a maximum diameter portion of the stent delivery system 1 at the side distal from the proximal-side tube 4. In other words, in the portion of the stent delivery system 1 positioned distally of the proximal-side tube 4, the maximum outer diameter is preferably greater than the outer diameter of the entire proximal-side tube 4. Therefore even in a state in which the guide wire extending toward the end proximal from the opening 23 is disposed along the side surface of the proximal-side tube 4, it is possible to make the outer diameter of the proximal-side tube 4 almost equal to the outer diameter of the maximum diameter portion of the stent delivery system 1 over the part distal from the proximal-side tube 4. Thus it is possible to insert the proximal-side tube 4 into a blood vessel having a relatively small diameter.

At the proximal portion of the proximal-side tube 4, the stent delivery system 1 of this embodiment includes a pulling wire winding mechanism for winding the pulling wire 6 and moving the stent accommodation tubular member 5 toward the proximal direction.

The stent delivery system 1 according to this embodiment includes the distal-side tube 2, the stent 3, the proximal-side tube 4, the stent accommodation tubular member 5, the pulling wire 6, the slide tube 7, the fixing tube 8, and an operation part 10 having the mechanism for winding the pulling wire 6. The fixing tube 8 connects the distal-side tube 2 and the proximal-side tube 4 to each other and is provided with the opening 23 communicating with the proximal portion of the distal-side tube 2.

Figure 3:
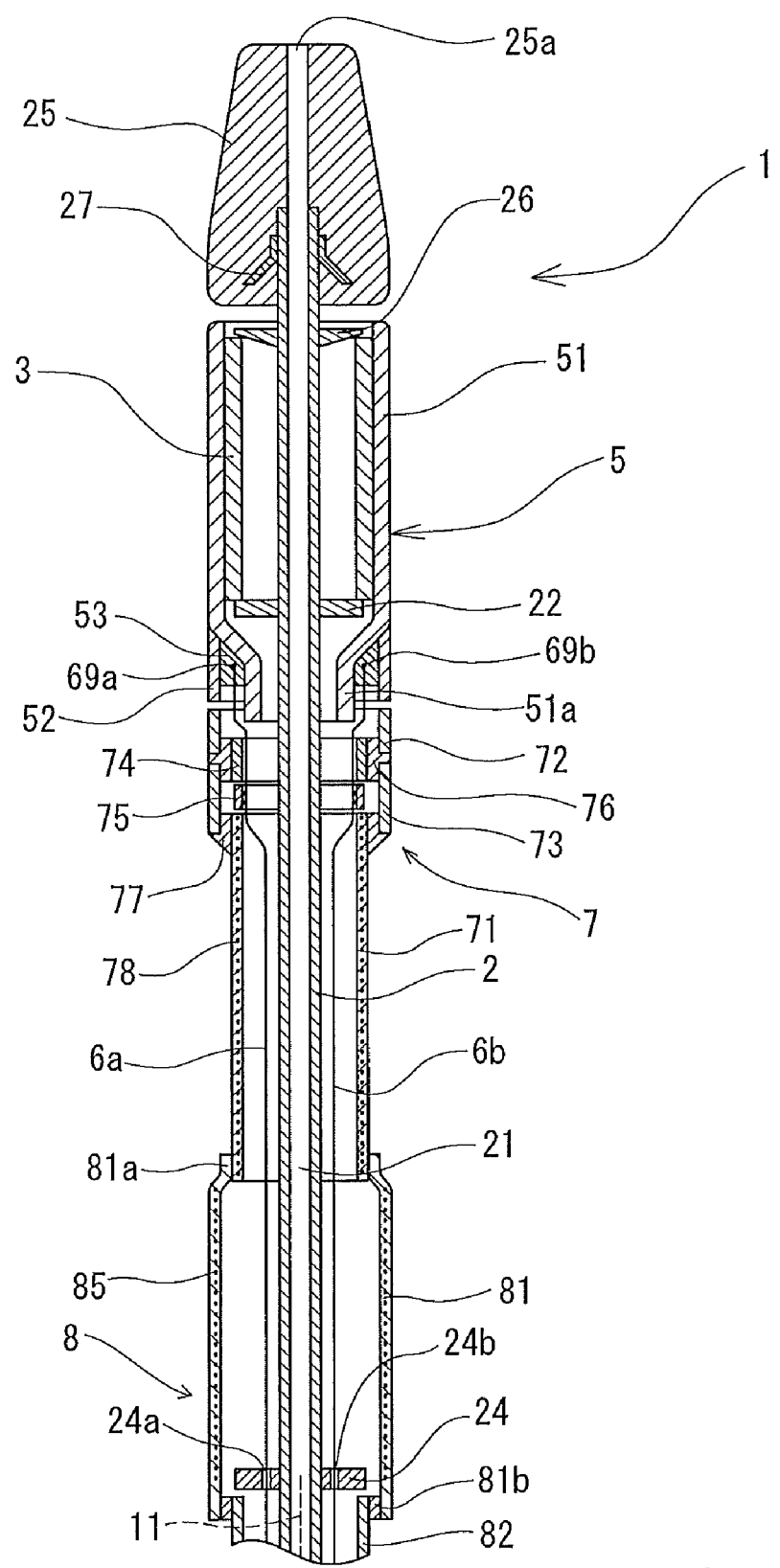
FIG. 3 is an enlarged cross-sectional view of the stent delivery system shown in FIG. 2.
Figure 4:
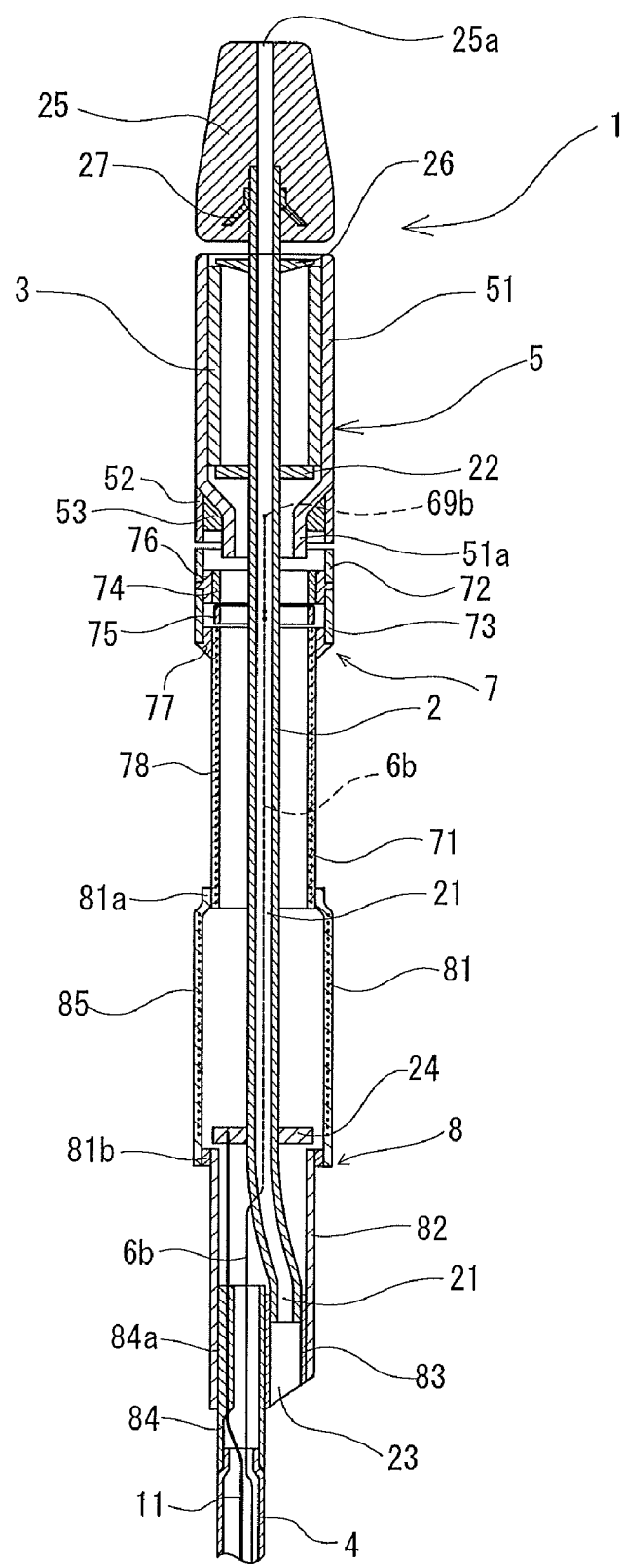
FIG. 4 is a cross-sectional view of the stent delivery system shown in FIG. 2 taken along the section line IV-IV in FIG. 2.
Figure 5:
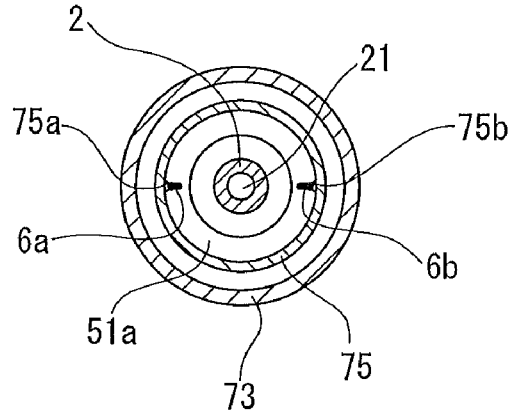
FIG. 5 is an enlarged cross-sectional view of the stent delivery system shown in FIG. 2 taken along the section line V-V of FIG. 2.
Figure 6:
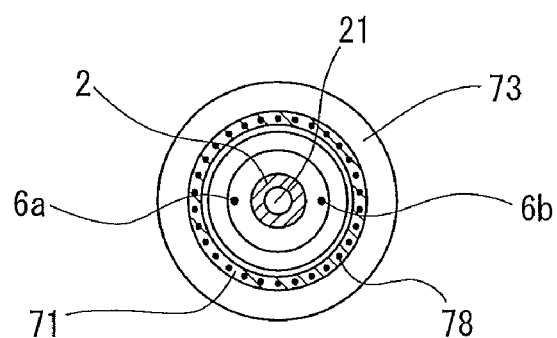
FIG. 6 is an enlarged cross-sectional view of the stent delivery system shown in FIG. 2 taken along the section line VI-VI of FIG. 2.

As shown in FIGS. 1-10, the distal-side tube 2 is a tubular body in which the guide wire lumen 21 penetrates through the distal-side tube 2 from its distal end to its proximal end so that the distal and proximal ends of the distal-side tube 2 are open. The distal portion of the distal-side tube 2 includes a distal-end member 25. The distal-end member 25 is fixed to the distal end of the distal-side tube 2 and possesses a distal-end opening 25a at the distal end of the distal-end member 25. The distal-end member 25 may be formed integrally with the distal-side tube 2. The proximal portion of the distal-side tube 2 is fixed to the fixing tube 8. As shown in FIG. 1, the proximal end of the distal-side tube 2 communicates with the opening 23 in the fixing tube 8 as shown in FIG. 4. The proximal portion of the distal-side tube 2 is curved. As shown in FIGS. 1 and 4, the opening 23 is formed obliquely so that it inclines toward the proximal side. Thereby it is easy to guide the guide wire.

As shown in the drawings, the distal-side tube 2 is a tubular body in which the guide wire lumen 21 extends throughout its length from its distal end to its proximal end. The outer diameter of the distal-side tube 2 is 0.3 to 2.0 mm, preferably 0.5 to 1.5 mm. The inner diameter of the distal-side tube 2 is 0.2 to 1.5 mm, preferably 0.3 to 1.2 mm. The length of the distal-side tube 2 is 20 to 700 mm, preferably 30 to 550 mm.

It is preferable that the distal-end member 25 is disposed at the side distal from the distal end of the stent accommodation tubular member 5 and tapered toward its distal end, thus gradually decreasing in outer diameter as shown in FIGS. 1-4. This configuration helps facilitate insertion of the stent delivery system into a stenosed portion. It is preferable that the distal-side tube 2 is provided with a stopper, disposed distally of the stent 3, for inhibiting or preventing movement of the stent accommodation tubular member 5 in the distal direction toward the distal end of the stent delivery system. In this embodiment, the proximal end of the distal-end member 25 is configured to be contacted by the distal end of the stent accommodation tubular member 5 and functions as the above-described stopper.

The outer diameter of the distal end of the distal-end member 25 is preferably 0.5 to 1.8 mm. The outer diameter of the portion of the distal-end member 25 having the maximum diameter is preferably 0.8 to 4.0 mm. The length of the distal-side tapered portion of the distal-end member 25 is preferably 2.0 to 20.0 mm.

As shown in FIGS. 3 and 4, the distal-side tube 2 includes the stent proximal portion-locking portion 22 located at a position spaced a predetermined distance from the distal end of the tube 2 to inhibit or prevent the stent 3 from moving in the proximal direction toward the proximal side. The locking portion 22 is preferably formed as an annular (radially outwardly extending) projection. A portion of the distal-side tube 2 distal from the stent proximal portion-locking portion 22 constitutes the stent accommodation portion. The outer diameter of the locking portion 22 is set so that the locking portion 22 contacts the proximal end of the compressed stent 3. When the stent accommodation tubular member 5 moves to the proximal side of the stent delivery system, the locking portion 22 maintains the position of the stent 3. Thereby the stent 3 is eventually discharged from the stent accommodation tubular member 5.

In the stent delivery system 1 of this embodiment, as shown in FIGS. 3 and 4, the distal-side tube 2 has a stent distal portion-locking portion 26 disposed at a position distal from the stent proximal portion-locking portion 22 and distally spaced from the stent proximal portion-locking portion 22 by a predetermined axial distance. As shown in FIGS. 3 and 4, the stent distal portion-locking portion 26 is preferably disposed slightly proximal of the distal end of the stent accommodation tubular member 5. The stent distal portion-locking portion 26 is preferably formed as an annular (radially outwardly extending) projection. The space between the stent distal portion-locking portion 26 and the stent proximal portion-locking portion 22 forms a stent accommodation portion. The outer diameter of the stent distal portion-locking portion 26 is so set that the stent distal portion-locking portion 26 contacts the distal end of the compressed stent 3. The diameter of the proximal surface of the stent distal portion-locking portion 26 decreases toward the proximal end of the stent distal portion-locking portion 26, thus forming a tapered surface. Therefore, while discharging the stent from the stent accommodation tubular member, the stent distal portion-locking portion 26 does not cause an interference and allows the stent delivery system 1 to be relatively easily removed (more specifically, accommodation in guiding catheter or sheath) after the stent 3 is discharged from the stent accommodation tubular member.

The outer diameter of the stent proximal portion-locking portion 22 and the outer diameter of the stent distal portion-locking portion 26 are preferably 0.8 to 4.0 mm. It is preferable that the stent proximal portion-locking portion 22 and the stent distal portion-locking portion 26 are formed as an annular projection (radially outwardly extending ring-shaped member) respectively, as shown in FIGS. 3 and 4. Provided that the stent proximal portion-locking portion 22 and the stent distal portion-locking portion 26 restrict the movement of the stent 3 and are individually capable of pressing the stent 3 out of the stent delivery system, the stent proximal portion-locking portion 22 and the stent distal portion-locking portion 26 may be formed as one or a plurality of circumferentially spaced projections integral with the distal-side tube 2 or separate from the distal-side tube 2. In addition, the stent proximal portion-locking portion 22 and the stent distal portion-locking portion 26 may be made of an x-ray contrast material separate from the distal-side tube. This would allow the position of the stent to be accurately grasped or assessed so that movement can be more easily accomplished. Examples of the x-ray contrast material include gold, platinum, platinum-iridium alloy, silver, stainless steel, and alloys of these metals. The projection can be mounted on the distal-side tube by forming a wire from the x-ray contrast material and winding the wire around the outer surface of the distal-side tube, or mounted on the distal-side tube by forming a pipe from the x-ray contrast material and caulking or bonding the pipe to the outer surface of the distal-side tube Materials for forming the distal-side tube are preferably materials having a proper degree of hardness and flexibility. For example, it is preferable to use polyolefin such as polyethylene, polypropylene; polyamide; polyester such as polyethylene terephthalate; fluorine-based polymer such as ETFE; PEEK (polyether ether ketone); and polyimide. Of the above-described resins, thermoplastic resin is preferable. Further, thrombosis-resistant materials may be applied to the outer surface of the distal-side tube exposed to the outside. As thrombosis-resistant materials, polyhydroxyethyl methacrylate, hydroxyethyl methacrylate-styrene copolymers (for example, HEMA-St-HEMA block copolymer), and the like can be preferably used.

When the distal-end member 25 is composed of a material separate from that of the distal-side tube 2, it is preferable to use flexible materials for the distal-end member 25. Examples include synthetic resin elastomers such as olefin elastomers (for example, polyethylene elastomer, polypropylene elastomer), polyimide elastomer, styrene elastomers, (for example, styrene-butadiene-styrene copolymer, styrene-isoprene-styrene copolymer, styrene-ethylene-butylene-styrene copolymer), polyurethane, urethane elastomers, and fluorine-based elastomers; and rubbers including synthetic rubber such as urethane rubber, silicone rubber, butadiene rubber, and natural rubber such as Latex rubber.

The stent delivery system 1 of this embodiment includes the distal-side tube 2 and the distal-end member 25 composed of separate members, and a stopping member 27 is fixed to the distal portion of the distal-side tube 2. The stopping member 27 has a tubular portion fixed to the distal-side tube 2 and a skirt portion which taperingly spreads outwardly in the proximal direction from the tubular portion. The stopping member 27 is embedded inside the distal-end member 25 to help prevent separation of the distal-end member 25 and movement of the distal-end member 25 toward the distal side. It is preferable to form the stopping member 27 of a metal (for example, stainless steel).

As shown in FIGS. 1, 2, and 4, the proximal-side tube 4 is a tubular body from its distal end to proximal end and has the operation part 10 fixed to its proximal end. The distal portion of the proximal-side tube 4 is joined to the fixing tube 8 by a fixing member 84. The proximal-side tube 4 is provided with a lumen into which the pulling wire 6 is inserted.

The length of the proximal-side tube 4 is 300 to 1500 mm, preferably 800 to 1300 mm. The outer diameter of the proximal-side tube 4 is 0.5 to 1.5 mm, preferably 0.6 to 1.3 mm. The inner diameter of the proximal-side tube 4 is 0.3 to 1.4 mm, preferably 0.5 to 1.2 mm. The interval (perpendicular distance) between the axis of the proximal-side tube 4 and the axis of the distal-side tube 2 is 0.1 to 2.0 mm, preferably 0.5 to 1.5 mm.

Materials for forming the proximal-side tube are preferably materials having a certain degree of hardness and flexibility. For example, it is preferable to use polyolefin such as polyethylene, polypropylene; nylon; polyethylene terephthalate; fluorine-based polymer such as ETFE; PEEK (polyether ether ketone); and polyimide. Further, thrombosis-resistant materials may be applied to the outer surface of the proximal-side tube. As thrombosis-resistant materials, it is possible to use polyhydroxyethyl methacrylate, hydroxyethyl methacrylate-styrene copolymers (for example, HEMA-St-HEMA block copolymer). Materials for forming the proximal-side tube 4 preferably include materials having a comparatively high rigidity. It is possible to use metal such as Ni—Ti, brass, stainless steel, aluminum, and the like; and resin having a comparatively high rigidity such as polyimide, vinyl chloride, polycarbonate, and the like.

Figure 10:
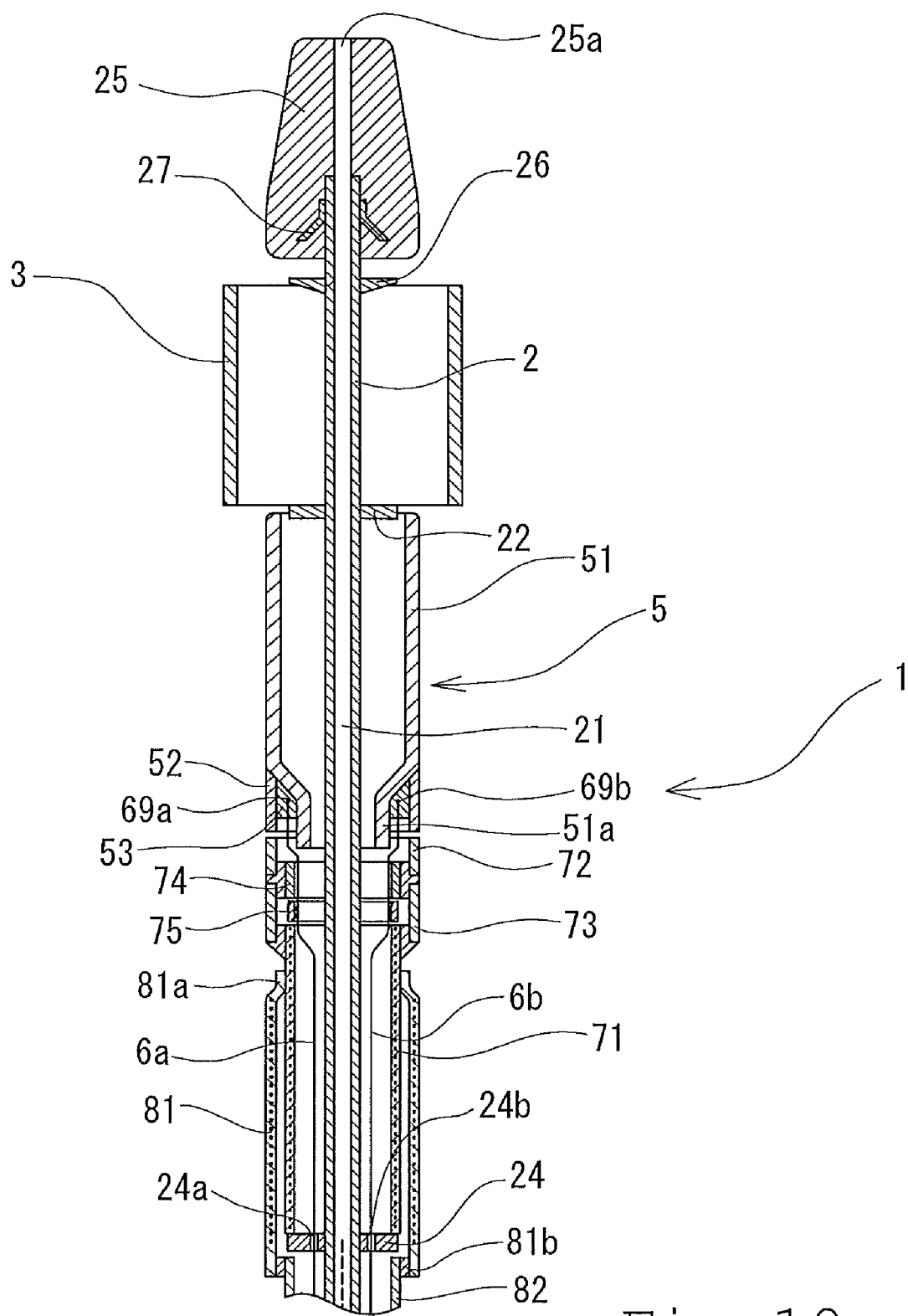
FIG. 10 is an cross-sectional view of the distal portion of the stent delivery system disclosed here, explaining the operation of the stent delivery system.

As shown in FIGS. 1-5 and 8, the stent accommodation tubular member 5 is a tubular body having a predetermined length. The stent accommodation tubular member 5 is open at its distal and proximal ends. When the stent 3 is implanted in a stenosed portion of a lumen, the opening of the stent accommodation tubular member 5 disposed at its distal end functions as a discharge opening of the stent 3. As shown in FIG. 10, upon being pressed out of the opening of the stent accommodation tubular member 5 disposed at its distal end, stress applied to the stent 3 is released and the stent expands, thus returning to its configuration before it was compressed.

The length of the stent accommodation tubular member 5 is preferably 20 mm to 400 mm, more preferably 30 mm to 250 mm. The outer diameter of the stent accommodation tubular member 5 is preferably 1.0 mm to 4.0 mm, more preferably 1.5 mm to 3.0 mm. The inner diameter of the stent accommodation tubular member 5 is preferably 1.0 to 2.5 mm.

The stent accommodation tubular member 5 is comprised of a tubular member body portion 51 having a smaller-diameter portion 51a at the proximal portion of tubular member body portion 51 and a tubular portion 52 enclosing or surrounding the small-diameter portion 51a. The proximal portion of the small-diameter portion 51a projects axially beyond the tubular portion 52 (i.e., the small-diameter portion 51a projects axially further in the proximal direction than the tubular portion 52). Distal portions 69a, 69b of the pulling wire 6a, 6b penetrate into a clearance between the outer periphery of the small-diameter portion 51a and the inner periphery of the tubular portion 52, and are fixed to the stent accommodation tubular member 5 with a fixing agent 53 located in the clearance. The fixing agent 53 constitutes a connecting means for connecting the pulling wire and the stent accommodation tubular member 5 so that the stent accommodation tubular member 5 is moved in the proximal direction when a pulling force in the proximal direction is applied to the pulling wire.

The small-diameter portion 51a has a tapered portion whose outer diameter gradually decreases toward the proximal end and a short cylindrical portion extending in the proximal direction from the tapered portion (on the proximal end of the tapered portion). The tubular portion 52 is fixed to the proximal portion of the tubular member body portion 51, with the tubular portion 52 enclosing the diameter-decreased portion (small-diameter portion) 51a of the tubular member body portion 51. Thus the small-diameter portion 51a of the tubular member body portion 51 forms an annular projection projecting into the tubular portion 52 and toward the proximal end of the tubular portion 52. An annular clearance portion is formed between the outer surface of the annular projection and the inner surface of the tubular member 52 (more specifically, distal portion of the small-diameter portion 51a).

In this embodiment, the distal portions 69a, 69b of the pulling wire 6a, 6b are effectively fixed to the outer surface of the small-diameter portion 51a. That is, the fixing agent is filled in the annular clearance portion to integrate the tubular member body portion 51 and the proximal-side tubular portion 52 with each other. With the fixing agent filled in the annular clearance portion, the distal portions (fixing point) 69a, 69b of the pulling wire 6a, 6b described later are fixed to the stent accommodation tubular member 5. As the fixing agent, it is preferable to use an adhesive agent such as epoxy resin, ultraviolet ray curing resin, and cyanoacrylate-based resin. Thermal fusion can be also used.

In the stent accommodation tubular member 5 used in this embodiment, the tubular member body portion 51 and the tubular portion 52 have almost an equal outer diameter. The outer diameter of the stent accommodation portion is preferably 1.0 to 4.0 mm, more preferably 1.5 to 3.0 mm. The length of the stent accommodation tubular member 5 is preferably 20 to 400 mm, more preferably 30 mm to 300 mm. The length of the tubular member body portion 51 is preferably 10 to 300 mm, more preferably 15 mm to 250 mm. The length of the proximal-side tubular portion 52 is preferably 10 to 300 mm, more preferably 15 mm to 250 mm.

The stent accommodation tubular member 5 is not limited to the above-described construction composed of the tubular member body portion 51 and the proximal-side tubular portion 52, as the stent accommodation tubular member 5 may be integrally formed as one piece (i.e., the tubular member body portion 51 and the proximal-side tubular portion 52 are integrally formed as a single unitary member).

The slide tube 7 is so disposed that the distal end of the slide tube 7 is proximate to the proximal end of the stent accommodation tubular member 5. The slide tube 7 can be accommodated inside the fixing tube 8 from the proximal side thereof. The slide tube 7 may be so constructed that it can enclose the fixing tube 8 from the distal side thereof. By pulling the pulling wire 6, the slide tube 7 is movable toward the proximal side together with the stent accommodation tubular member 5. The slide tube 7 is not fixed to the stent accommodation tubular member 5.

The stent delivery system 1 of this embodiment includes the ring-shaped member 75 which is accommodated inside the slide tube 7 in an unfixed state and moves together with the slide tube 7. The pulling wires 6a, 6b are fixed to the inner surface of the ring-shaped member 75.

The inventors here have found that to keep pulling the pulling wire, it is preferably important to untwist the distal portion of the pulling wire connected to the stent accommodation tubular member when a stent delivery system insertion operation is performed to effect an excellent pulling operation. But it is necessary that the pulling wire can be pulled. Fixing of the pulling wire to a portion other than the stent accommodation tubular member can cause interference in the pulling operation.

With this as the case, it is preferable to provide the stent delivery system 1 with the ring-shaped member 75 which is accommodated inside the slide tube 7 and moves together with the slide tube 7 to fix the pulling wires 6a, 6b to the ring-shaped member 75 as is the case with the stent delivery system 1 of this embodiment.

With this arrangement, while inserting the stent delivery system into an organism, a twisted force imparted at the proximal portion of the stent delivery system causes the distal portion of the pulling wire connected to the stent accommodation tubular member to be twisted to a relatively very low extent. This helps ensure a preferable pulling operation.

In the stent delivery system 1 of this embodiment, the ring-shaped member 75 is accommodated inside the slide tube 7 in an unfixed state. Therefore the fixing portion does not cause interference in pulling the pulling wire. Further the ring-shaped member is not fixed to the slide tube. Thus even though a twist force imparted to the proximal portion of the stent delivery system is transmitted to the slide tube, the pulling wire is capable of holding a preferable state without generating problematic twist.

The slide tube 7 has a ring-shaped member-holding portion allowing the ring-shaped member 75 to rotate while preventing it from axially moving. Because the ring-shaped member 75 is rotatable relative to the slide tube 7, it is difficult for the ring-shaped member 75, the fixing portion of the pulling wire, and the pulling wire to follow the rotation of the slide tube 7.

Figure 7:
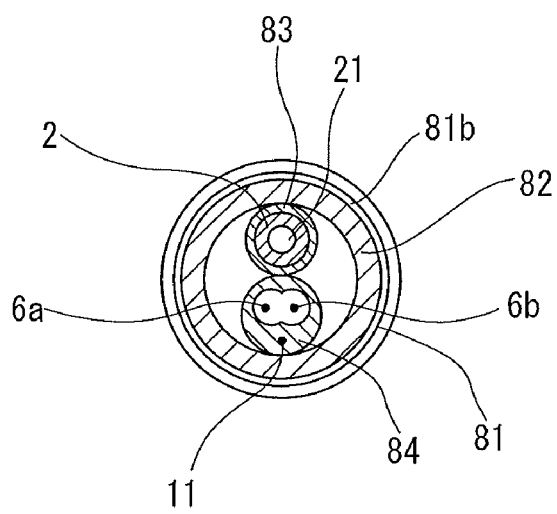
FIG. 7 is an enlarged cross-sectional view of the stent delivery system shown in FIG. 2 taken along the section line VII-VII of FIG. 2.
Figure 8:
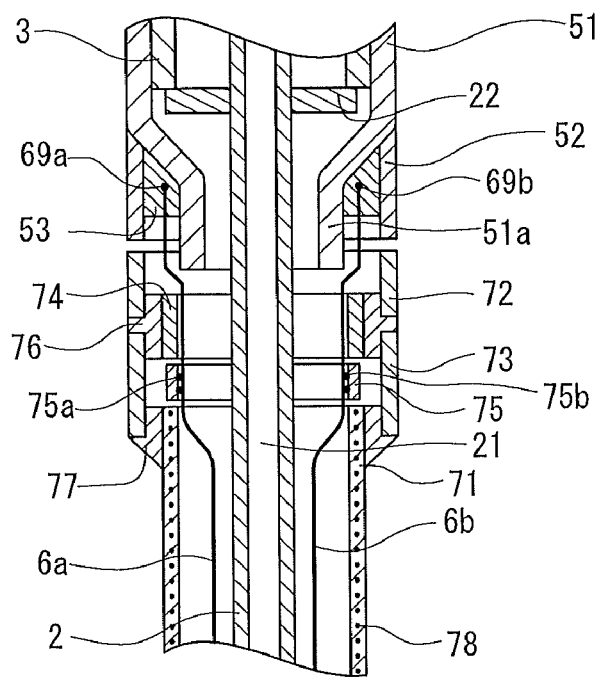
FIG. 8 is an enlarged cross-sectional view of a proximal portion of the stent accommodation tubular member of the stent delivery system of FIG. 1 and a distal portion of the slide tube of the stent delivery system of FIG. 1.

As shown in FIGS. 2-7, the slide tube 7 includes a slide tube body 71 and a distal-side member (72, 73) which is fixed to the distal end of the slide tube body 71 and has outer and inner diameters larger than those of the slide tube body 71. In this embodiment, as shown in FIG. 8, the distal-side member of the slide tube 7 includes: an outer tubular part constructed of a first tubular member 72 and a second tubular member 73; an inner tubular part constructed of a third tubular member 74 disposed inside the proximal portion of the first tubular member 72 and the distal portion of the second tubular member 73; and a fixing part 76 fixing the outer tube and the inner tube together and to the fixing part. In other words, the fixing part 76 fixes the first tubular member 72, the second tubular member 73, and the third tubular member 74 together and to the fixing part 76. The second tubular member 73 has outer and inner diameters almost equal to those of the tubular member 72. The proximal portion of the second tubular member 73 constructing the outer tube is fixed to the distal portion of the slide tube body 71 by a fixing portion 77. The distal portion of the slide tube body 71 penetrates into the proximal portion of the second tubular member 73 forming a part of the outer tube, and is axially spaced a predetermined axial distance from the proximal portion of the third tubular member 74 forming the inner tube. Thereby, an annular concavity constituting the ring-shaped member-holding portion is formed by the distal portion of the slide tube body 71, the inner surface of the second tubular member 73 constituting the outer tube, and the proximal portion of the third tubular member 74 constituting the inner tube. The ring-shaped member 75 is accommodated inside the annular concavity constituting the ring-shaped member-holding portion. Because the ring-shaped member 75 is not fixed to the slide tube body 71, the second tubular member 73, or the third tubular member 74, the ring-shaped member 75 is rotatable. But the ring-shaped member 75 is incapable of axially moving inside the slide tube 7 except for a clearance such as illustrated.

A metal ring is preferably used for the ring-shaped member 75. As shown in FIG. 8, the pulling wire 6*a*, 6*b* is fixed to the inner surface of the ring-shaped member 75 by fixing portions 75*a*, 75*b*. As the fixing portions, it is preferable to use welding or an adhesive agent to fix the pulling wires 6*a*, 6*b* to the fixing portions. Because the pulling wires 6*a*, 6*b* are fixed to the ring-shaped member 75, by pulling the pulling wires 6*a*, 6*b*, the ring-shaped member 75 is pulled. The slide tube 7 is moved toward the proximal side of the stent delivery system 1 by being pressed from the distal side by the ring-shaped member 75.

It is preferable that the distal portion of the slide tube 7 encloses the proximal portion of the small-diameter portion 51*a* of the stent accommodation tubular member 5. It is also preferable that the slide tube 7 and the stent accommodation tubular member 5 are not joined with each other. In this embodiment, as shown in FIGS. 4 and 8, the distal portion of the slide tube 7 encloses the proximal portion of the small-diameter portion 51*a* of the stent accommodation tubular member 5 without being joined with the proximal portion of the small-diameter portion 51*a* and without substantially contacting the proximal portion of the small-diameter portion 51*a*. More specifically, the distal portion of the first tubular member 72 constituting a part of the outer tube encloses the proximal portion of the small-diameter portion 51*a* of the stent accommodation tubular member 5 without substantially contacting the proximal portion of the small-diameter portion 51*a*.

In this embodiment, the slide tube 7 includes a reinforcing layer 78 over the entire slide tube body 71. By providing the slide tube 7 with such a reinforcing layer, kink resistance is improved and the slide tube 7 slides favorably. It is preferable that the reinforcing layer is reticulated.

It is preferable that the reticulated reinforcing layer is made of a braided wire. For example, the reticulated reinforcing layer is made of braided wire of a metal such as stainless steel, an elastic metal, a superelastic alloy or a shape memory alloy having a diameter of 0.01 to 0.2 mm, preferably 0.02 to 0.15 mm. Alternatively the reticulated reinforcing layer may be formed of synthetic fiber such as polyamide fiber, polyester fiber, and polypropylene fiber.

As shown in FIGS. 2-4, 7 and 9, in the stent delivery system 1 of this embodiment, the fixing tube 8 has a distal-side fixing tube 81 having a relatively larger outer diameter and a proximal-side fixing tube 82 fixed to the proximal portion of the distal-side fixing tube 81 and having a relatively smaller outer diameter. The distal-side fixing tube 81 has a distal end diameter-decreased portion 81*a*. The inner surface of the distal end diameter-decreased portion 81*a* is in contact with the outer surface of the proximal portion of the slide tube 7. The slide tube 7 is not fixed to the distal-side fixing tube 81, but slides toward the proximal side, thereby penetrating into, and being accommodated in, the distal side fixing tube 81. The slide tube 7 moves in the proximal direction relative to the fixing tube 8 when the pulling wire 6 is pulled in the proximal direction, and this causes axial overlap between the slide tube 7 and the fixing tube 8 that increases with continued movement of the slide tube 7 in the proximal direction relative to the fixing tube 8.

It is preferable that the slide tube 7 is of a type that is accommodated inside the fixing tube 8, but the type of the slide tube is not limited in this manner. The slide tube 7 may be of a type in which the slide tube slides toward the proximal side and so the fixing tube is enclosed inside the slide tube.

Figure 9:
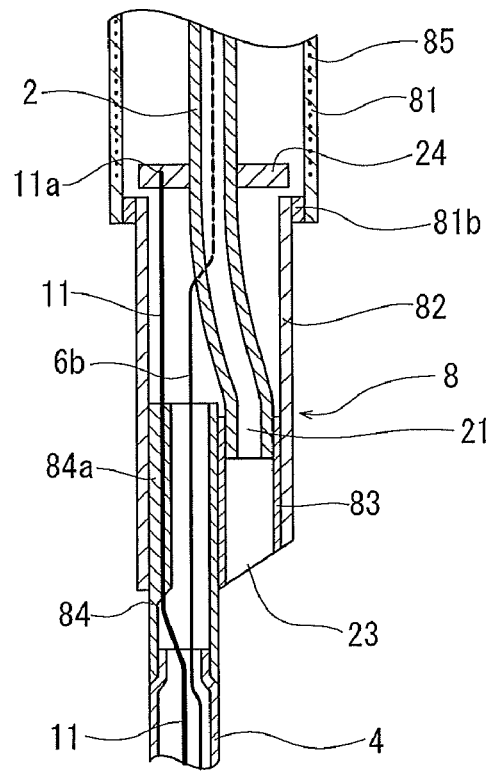
FIG. 9 is an enlarged cross-sectional view of a proximal portion of a fixing tube of the stent delivery system of FIG. 1.

The distal portion of the proximal-side fixing tube 82 penetrates into the proximal end of the distal-side fixing tube 81. The distal portion of the proximal-side fixing tube 82 is fixed to the proximal end of the distal-side fixing tube 81 by the fixing portion 81*b*. A slide tube-locking portion 24 is provided on the outer surface of the distal-side tube 2 with the slide tube-locking portion 24 disposed inside the fixing tube 8. More specifically as shown in FIG. 9, the slide tube-locking portion 24 is provided at a position axially corresponding to the proximal portion of the distal-side fixing tube 81. The slide tube 7 is slidable in the proximal direction until the slide tube 7 contacts the slide tube-locking portion 24. In other words, when the slide tube 7 contacts the slide tube-locking portion 24, the slide tube 7 is prevented from further moving toward the proximal side beyond the slide tube-locking portion 24.

In this embodiment, as shown in FIG. 9, the distal side portion of the fixing tube 8 is reinforced. More specifically, the distal-side fixing tube 81 has a reinforcing layer 85 over almost its entire length. It is preferable that the reinforcing layer is reticulated, spiral or the like. A reticulated reinforcing layer is especially preferable. It is preferable that the reticulated reinforcing layer is formed using a fine metal wire. Stainless steel is a preferable fine metal wire. As shown in FIG. 9, it is preferable that the reinforcing layer is not present at a portion where the distal-side fixing tube 81 is connected with the proximal-side fixing tube 82 (i.e., the reinforcing layer is not present at the proximal-most end portion of the distal-side fixing tube 81).

The proximal portion of the distal-side tube 2 is provided with a tubular fixing member 83 accommodating the proximal portion of the distal-side tube 2. The tubular fixing member 84 is also positioned at the distal end of the proximal-side tube 4. As shown in FIGS. 7 and 9, the tubular fixing member 83 and the tubular fixing member 84 axially overlap one another and are fixed to the (interior of) proximal-side fixing tube 82.

As shown in FIGS. 2 and 3, the stent delivery system 1 has a plurality, two in this illustrated embodiment, of the pulling wires 6*a*, 6*b*. The fixing points 69*a*, 69*b* of the pulling wires 6*a*, 6*b* are fixed radially outside the small-diameter portion of the stent accommodation tubular member 5 by the fixing agent 53 in a clearance of the tubular member 5. The pulling wires 6a, 6b are spaced from each other at a predetermined length. The fixing points 69a and 69b are also spaced from each other at a predetermined distance.

With respect to materials for forming the stent accommodation tubular member 5 (tubular member body portion 51, proximal-side tubular portion 52), the slide tube 7 (slide tube body 71), and the fixing tube 8 (distal-side fixing tube 81, proximal-side fixing tube 82), and considering the properties (flexibility, degree of hardness, strength, sliding property, kink resistance, and elasticity) desired or demanded for the stent accommodation tubular member, the materials are preferable selected appropriately from among polyethylene, polypropylene, nylon, polyethylene terephthalate, polyimide, and fluorine-based polymer such as PTFE, ETFE; and thermoplastic elastomer. The thermoplastic elastomer is appropriately selected from among nylon family (for example, polyamide elastomer), urethane family (for example, polyurethane elastomer), polyester family (for example, polyethylene terephthalate elastomer), olefin family (for example, polyethylene elastomer, polypropylene elastomer).

It is preferable to treat the outer surface of the stent accommodation tubular member 5 so that the outer surface displays lubricity. As such treatment, for example, methods of applying or fixing hydrophilic polymers such as polyhydroxyethyl methacrylate, polyhydroxyethyl acrylate, hydroxypropyl cellulose, methyl vinyl ether-maleic anhydride copolymer, polyethylene glycol, polyacrylamide, polyvinyl pyrrolidone to the outer surface thereof are listed. The above-described substances may be applied or fixed to the inner surface of the stent accommodation tubular member 5 to enhance slidability to the stent 3.

The stent accommodation tubular member 5 may be formed in a two-layer construction by using the above-described polymers (for example, outer layer is made of nylon, and inner layer is made of PTFE).

The stent delivery system 1 includes the pulling wire having one end fixed to the proximal portion of the stent accommodation tubular member 5 and which extends beyond the proximal end of the stent accommodation tubular member 5, extends through the slide tube 7 and the fixing tube 8, and extends inside the proximal-side tube 4. Pulling the pulling wire in the proximal direction or toward the proximal side of the proximal-side tube causes the stent accommodation tubular member 5 and the slide tube 7 to move in the proximal direction toward the proximal side.

In the illustrated embodiment shown in FIGS. 1, 2, 5-8 and 10, the stent delivery system 1 includes a plurality of pulling wires 6a, 6b fixed to the proximal portion of the stent accommodation tubular member 5 at the fixing points 69a, 69b disposed at positions considerably near the stent. In this embodiment, two pulling wires 6a, 6b are provided. The pulling wires 6a and 6b are spaced from each other at a predetermined distance. The fixing points 69a, 69b are also spaced from each other at a predetermined distance.

In this embodiment, as shown in FIG. 8 and as described above, the pulling wires 6a, 6b are fixed to the inner surface of the ring-shaped member 75 provided for the slide tube 7 at fixing points 75a, 75b respectively. The ring-shaped member 75 constitutes means for connecting the wire 6 to the slide tube 7 in a manner that the slide tube 7 is moved in the proximal direction when a pulling force is applied to the pulling wire 6 in the proximal direction. In the stent delivery system 1 of this embodiment, by pulling the pulling wires 6a, 6b toward the proximal side or in the proximal direction, the ring-shaped member 75 is pulled toward the proximal side, and the slide tube 7 (slide tube body 71) is contacted by the ring-shaped member 75. Thereby the slide tube 7 is also pulled to the proximal side. Thus in this embodiment, the stent accommodation tubular member 5 and the slide tube 7 are separately pulled, and at a pulling time, the stent accommodation tubular member 5 and the slide tube 7 do not contact each other. Because a force applied when the pulling wires 6a, 6b are pulled is distributed to the fixing points 69a, 69b and the fixing points 75a, 75b of the ring-shaped member 75, a fixed state between the pulling wires 6a, 6b and the stent accommodation tubular member 5 at the fixing points 69a, 69b is reliably inhibited or prevented from being released.

In the stent delivery system 1 of this embodiment, as shown in FIG. 1, the pulling wire penetrates through the proximal-side tube 4 and extends to the outside from the proximal end of the proximal-side tube.

Examples of materials for forming the pulling wire include a single wire material. Alternatively, a plurality of twisted wire materials can be preferably used. The diameter of the pulling wire is not limited to a specific diameter, but is normally and preferably 0.01 to 0.55 mm and more preferably 0.1 to 0.3 mm.

Examples of the materials for forming the pulling wire include a stainless steel wire (preferably, high-tensile stainless steel wire for spring), a music wire (preferably, a nickel-plated or chromium-plated music wire), a superelastic alloy wire, wires made of metals such as a Ni—Ti alloy, a Cu—Zn alloy, a Ni—Al alloy, tungsten, a tungsten alloy, titanium, a titanium alloy, a cobalt alloy, and tantalum, comparatively high-rigidity polymeric materials such as polyamide, polyimide, ultra-high-molecular-weight polyethylene, polypropylene, and fluorine-based resin; and combinations of these substances.

Resin having low frictional property which increases lubricity may be applied to the side surface of the pulling wire. Resins having low frictional property and suitable for use here include fluorine-based resin, nylon 66, polyether ether ketone, high-density polyethylene, and the like. The fluorine-based resin is more preferable than other resins. As the fluorine-based resin, polytetrafluoroethylene, polyvinylidene fluoride, ethylenetetrafluoroethylene, perfluoroalkoxy resin, and the like are examples. Coating may be accomplished with silicone or various hydrophilic resins.

The stent delivery system 1 of this embodiment has a rigidity-imparting member 11 that is separate from, and in addition to, the pulling wire. As shown in FIGS. 1-4, 7 and 9, the rigidity-imparting member 11 extends from the proximal side of the stent delivery system 1, passes through the proximal-side tube 4, and extends into the fixing tube 8. As shown in FIG. 9, a distal end 11a of the rigidity-imparting member 11 is fixed to the slide tube-locking portion 24. It is preferable that the distal end 11a of the rigidity-imparting member is fixed to the slide tube-locking portion 24 by embedding the distal end 11a of the rigidity-imparting member in a material forming the slide tube-locking portion 24. As shown in FIG. 3, the pulling wires 6a, 6b are not fixed to the slide tube-locking portion 24, but pass through passages 24a, 24b respectively.

In the stent delivery system 1 of this embodiment, as shown in FIG. 9, the rigidity-imparting member 11 is also fixed to the tubular fixing member 84 fixed to the fixing tube 8. As shown in FIG. 9, the tubular fixing member 84 is provided with a rigidity-imparting member-fixing portion 84a axially extended over a predetermined distance. By fixing the distal portion of the rigidity-imparting member 11 at two positions, a relatively high reinforcing effect is displayed by the distal portion of the rigidity-imparting member 11. Particularly the distal portion of the rigidity-imparting member 11 reinforces the slide tube-locking portion 24, when the slide tube 7 contacts the slide tube-locking portion 24.

It is preferable that the rigidity-imparting member 11 is fixed to the proximal portion of the proximal-side tube 4 or the operation part 10 described later at the proximal portion thereof. By providing the stent delivery system with the rigidity-imparting member 11, it is possible to help restrain the stent delivery system from deforming when the pulling member (pulling wire) is pulled. The distal end 11a of the rigidity-imparting member 11 may be formed as a flat portion so that the distal end 11a of the rigidity-imparting member 11 is securely fixed by the slide tube-locking portion 24. A wavy portion may be formed on the side surface of the rigidity-imparting member 11 to prevent the rigidity-imparting member 11 from slipping off the fixing member.

A single wire material or a plurality of twisted wire materials can be preferably used as the material for forming the rigidity-imparting member 11. Although the diameter of the rigidity-imparting member 11 is not limited to a specific diameter, the diameter of the rigidity-imparting member is normally 0.01 to 1.5 mm and preferably 0.1 to 1.0 mm.

It is preferable that the body-side portion (more specifically, the portion disposed inside proximal-side tube) of the rigidity-imparting member 11 has a relatively high rigidity (for example, the diameter of wire is relatively large), whereas the distal portion of the rigidity-imparting member has a relatively low rigidity (for example, the diameter of the wire is relatively small). It is preferable that the change point between both portions is disposed at a tapered portion where the diameter of the rigidity-imparting member 11 taperingly changes.

Examples of materials for forming the rigidity-imparting member 11 include a stainless steel wire (preferably, high tensile stainless steel wire for spring), a music wire (preferably, nickel-plated or chromium-plated music wire), a superelastic alloy wire, and wires made of metals such as a Ni—Ti alloy, a Cu—Zn alloy, a Ni—Al alloy, tungsten, a tungsten alloy, titanium, a titanium alloy, a cobalt alloy, and tantalum. It is preferable that the rigidity-imparting member 11 is harder than the pulling member (pulling wire).

The stent 3 is accommodated inside the stent accommodation tubular member 5.

As the stent 3, it is possible to use any types of self-expandable stents. For example, it is possible to preferably use the stent 3 having a configuration shown in FIG. 16 (showing a state in which by its expansion, the stent returns to a configuration before it is compressed). The stent 3 of this example has a cylindrical frame body 30, openings 34 partitioned (surrounded) or bounded by frames 36a, 36b constructing the cylindrical frame body 30, and cut-out portions 35 partitioned from one another with the frames 36a. The frame body 30 has opposite ends 33a, 33b.

Examples of materials for forming the stent, include synthetic resins or metals. Synthetic resin having a certain degree of hardness and elasticity is used. Synthetic resin compatible with organisms is preferable. More specifically, examples include polyolefin (for example, polyethylene, polypropylene), polyester (for example, polyethylene terephthalate), fluorine-based resin (for example, PTFE, ETFE), and materials, to be absorbed into organisms, such as polylactic acid, polyglicolic acid, and polylactic acid-polyglicolic acid copolymer. Metals compatible with organisms are preferable. Stainless steel, tantalum and a nickel-titanium alloy are examples. Superelastic metals are especially preferable. It is preferable that the stent 3 is formed integrally in one piece at the same time without forming change points at which properties might change rapidly. The stent is formed by preparing a metal pipe having an outer diameter suitable for a desired portion in an organism at which the stent is implanted, removing a part of the side surface of the metal pipe by cutting work (for example, mechanical cutting, laser machining, etc.), chemical etching or the like, and forming a plurality of cut-out portions or openings on the side surface.

Because the stent 3 has the cut-out portions 35 at the ends of the frame body 30, the ends 33a, 33b of the stent 3 deform relatively easily. Particularly the ends 33a, 33b are capable of partly deforming. The stent 3 thus has a favorable response to deformation of a blood vessel in which the stent 3 is implanted. Because the ends 33 are formed of the ends of a plurality of the frames 36a, the stent 3 is not broken easily and thus has a sufficient strength. The openings 34 surrounded or bounded by the frames 36a, 36b are formed between both ends 33a, 33b and deform easily owing to deformation of the frame 36a. Thus the stent 3 deforms easily at its central portion (central portion of the frame body 30). The configuration and number of cut-out portions and the openings are not limited to those shown in the drawing. However, the number of cut-out portions is preferably 3 to 10, and the number of openings is preferably 3 to 10.

The outer diameter of the frame body 30 is 2.0 mm to 30 mm, preferably 2.5 mm to 20 mm. The inner diameter of the frame body 30 (the inner diameter of the stent) is 1.4 mm to 29 mm, preferably 1.6 mm to 28 mm. The length of the frame body or stent is 10 to 300 mm, preferably 15 to 200 mm.

Figure 16:
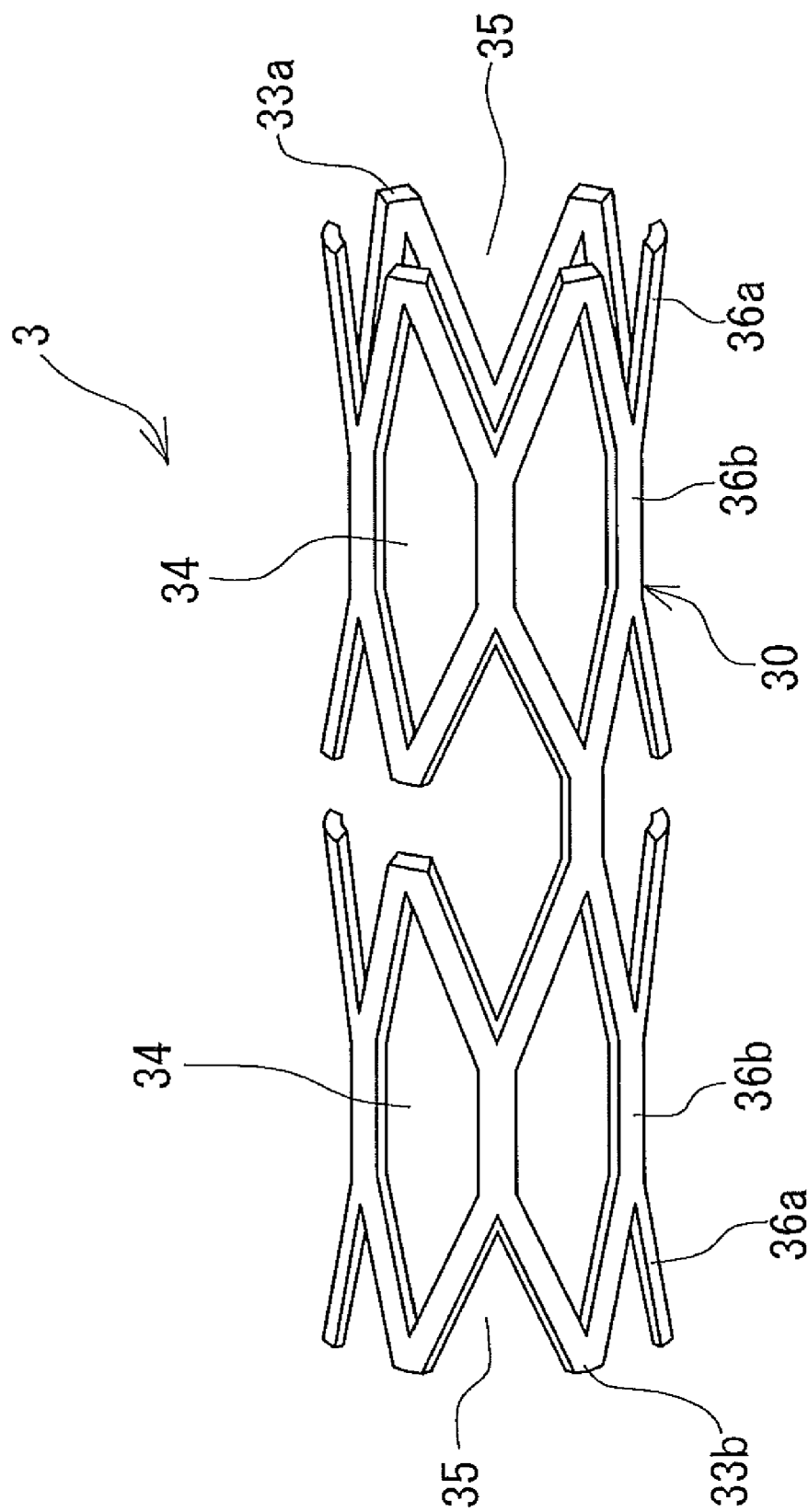
FIG. 16 is a perspective view of an example of a stent to be used in the stent delivery system disclosed here.

The configuration of the stent is not limited to the one shown in FIG. 16. For example, the stent may have trapezoidal-shaped cut-out portions at both ends of the stent, and a plurality of hexagonal openings at the central portion of the stent. As another example, the stent may have a rectangular cut-out portion at both ends of the stent and a plurality of rectangular (twice as long as length of cut-out portion) openings formed at the central portion of the stent. As still another configuration of the stent 3, it is possible to use a stent which can be decreased in its diameter at the time of insertion and can be expanded in diameter (restored to its original state) at the time of releasing the stent in the organism. The configuration of the stent is not limited to the above-described stents. For example, it is possible to use coiled stents, cylindrical stents, roll-shaped stents, various shaped tubular stents, higher-order coil-shaped stents, leaf spring-like stents, basket-shaped stents, and mesh-shaped stents.

Superelastic alloys are preferably used as the superelastic metal forming the stent. Herein, superelastic alloy refers to a so-called shape memory alloy that shows superelasticity essentially at the temperature (in the vicinity of 37° C.) of the organism. Examples of superelastic metals include a Ti—Ni alloy of 49-53 atomic percent of Ni, a Cu—Zn alloy of 38.5-41.5 wt % of Zn, a Cu—Zn—X alloy of 1-10 wt % of X (X=Be, Si, Sn, Al, Ga), and a Ni—Al alloy of 36-38 atomic percent of Al. The Ti—Ni alloy is preferably used. The mechanical characteristics of the Ti—Ni alloy can be appropriately changed by replacing a part of the Ti—Ni alloy with 0.01-10.0% of X to obtain a Ti—Ni—X alloy (X=Co, Fe, Mn, Cr, V, Al, Nb, W, B and the like), by replacing a part of the Ti—Ni alloy with 0.01-30.0 atomic percent of X to obtain a Ti—Ni—X alloy (X=Cu, Pb, Zr) or by selecting a cold working ratio or/and the condition of final heat treatment. Furthermore the mechanical characteristics of the Ti—Ni—X alloy can be appropriately changed by selecting the cold working ratio or/and the condition of final heat treatment.

The buckling strength (yield stress when load is applied) of the superelastic alloy to be used is 5-200 kgf/mm$^2$ (22° C.), preferably 8-150 kg/mm². The restoring stress (yield stress when load is eliminated) of the superelastic alloy is 3-180 kg/mm² (22° C.), preferably 5-130 kg/mm². Superelasticity means that when a metal is deformed (bent, stretched, compressed) to a region in which a normal metal deforms plastically at a service temperature, the metal returns to its original configuration substantially without heating it after a deformed state is released.

The stent to be used in the stent delivery system disclosed here may have a diameter-reducible stent body formed approximately cylindrically and a cylindrical cover (not shown) sealing the side surface of the stent body.

The stent delivery system disclosed here is not limited to the embodiments described above. For example, the stent delivery system here may have a construction similar to that of a stent delivery system 20 shown in FIG. 11.

Figure 11:
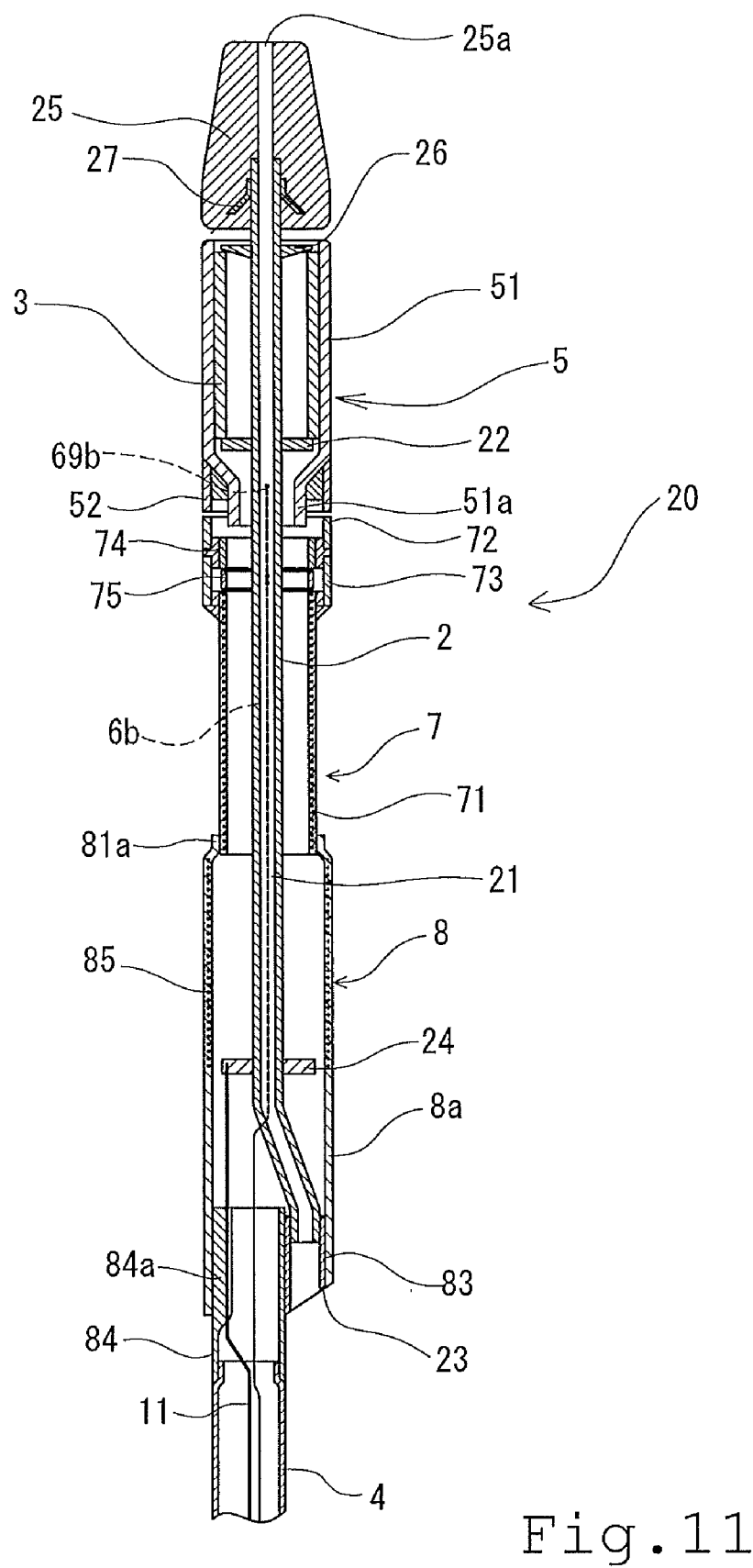
FIG. 11 is an enlarged cross-sectional view of the distal portion of a stent delivery system of another embodiment disclosed here.

In the stent delivery system 20 of this embodiment, unlike the above-described stent delivery system 1, the fixing tube 8 is not comprised of the combination of the distal-side fixing tube 81 and the proximal-side fixing tube 82. Instead, the FIG. 11 embodiment of the stent delivery system 20 includes an integrally formed, unitary, one-piece fixing tube 8a. As shown in FIG. 11, the fixing tube 8a has a reinforcing layer 85 extending from the distal side to the neighborhood of a position where the slide tube-locking portion 24 is disposed. The reinforcing layer 85 is the same as the above-described reinforcing layer.

Figure 12:
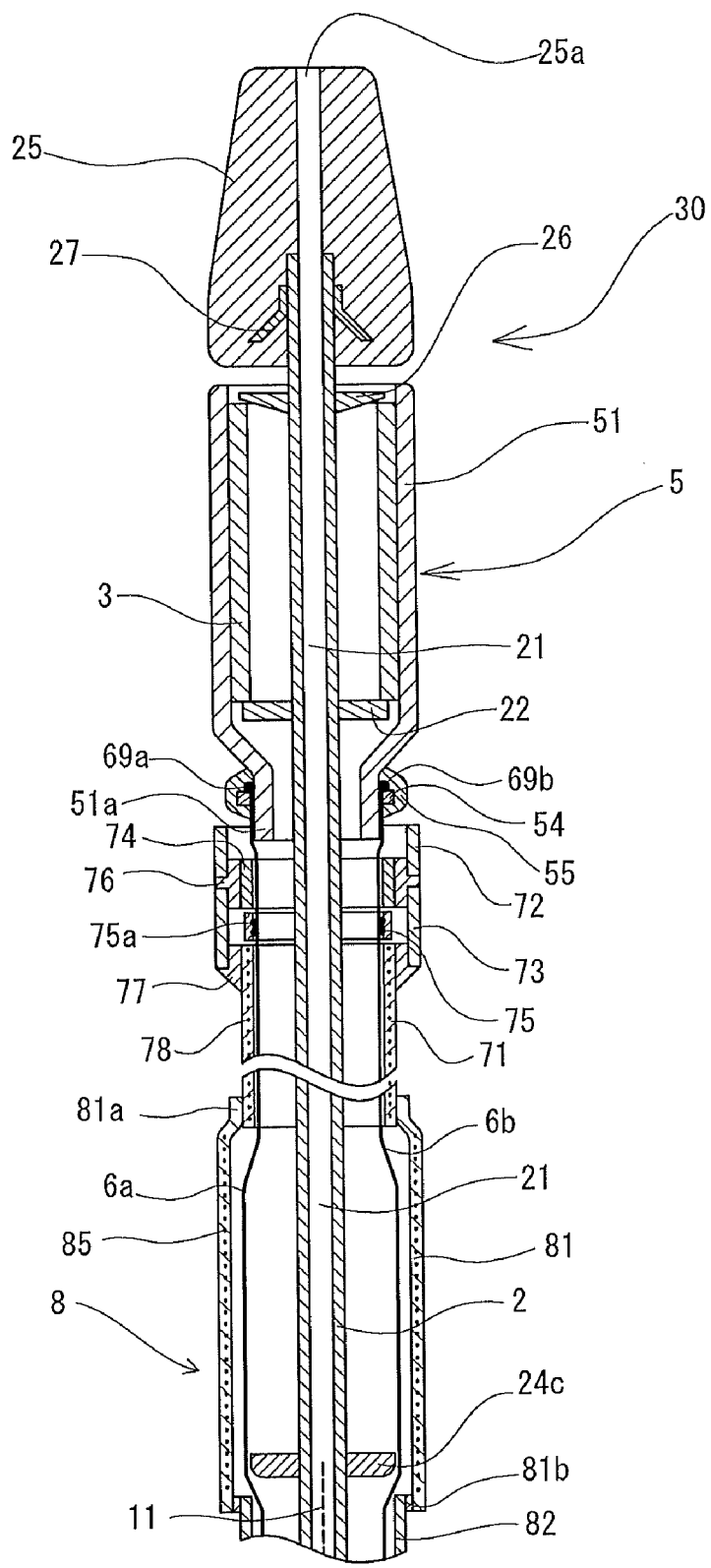
FIG. 12 is an enlarged cross-sectional view of the distal portion of a stent delivery system according to another embodiment disclosed here.

All embodiments of the stent delivery system described above can be modified to include a construction similar to that of the stent delivery system 30 shown in FIG. 12. In the stent delivery system 30 of this embodiment, the distal portions (69a, 69b) of the pulling wires 6a, 6b are fixed by a metal ring (ring-shaped or annular member) 54 fixed to the small-diameter portion 51a of the stent accommodation tubular member 5. A covering portion 55 of resin or the like is disposed on the outer surface of the metal ring 54 to prevent the metal ring 54 and the distal end of the pulling wires 6a, 6b from being exposed or released. The member 54 and the covering portion 55 constitute a connecting means for connecting the pulling wire and the stent accommodation tubular member 5 so that the stent accommodation tubular member 5 is moved in the proximal direction when a pulling force in the proximal direction is applied to the pulling wire. The stent delivery system 30 of this embodiment does not have the tubular portion 52 provided in the earlier-described embodiment of the stent delivery system 1.

The stent delivery systems of all of the above-described embodiments may have a construction similar to that of the stent delivery system 30 shown in FIG. 12. Here, a slide tube-locking portion 24c is constructed so that it does not include a passage through which passes the pulling wires 6a, 6b. In this arrangement, the pulling wires 6a, 6b pass outside the slide tube-locking portion 24c.

Figure 13:
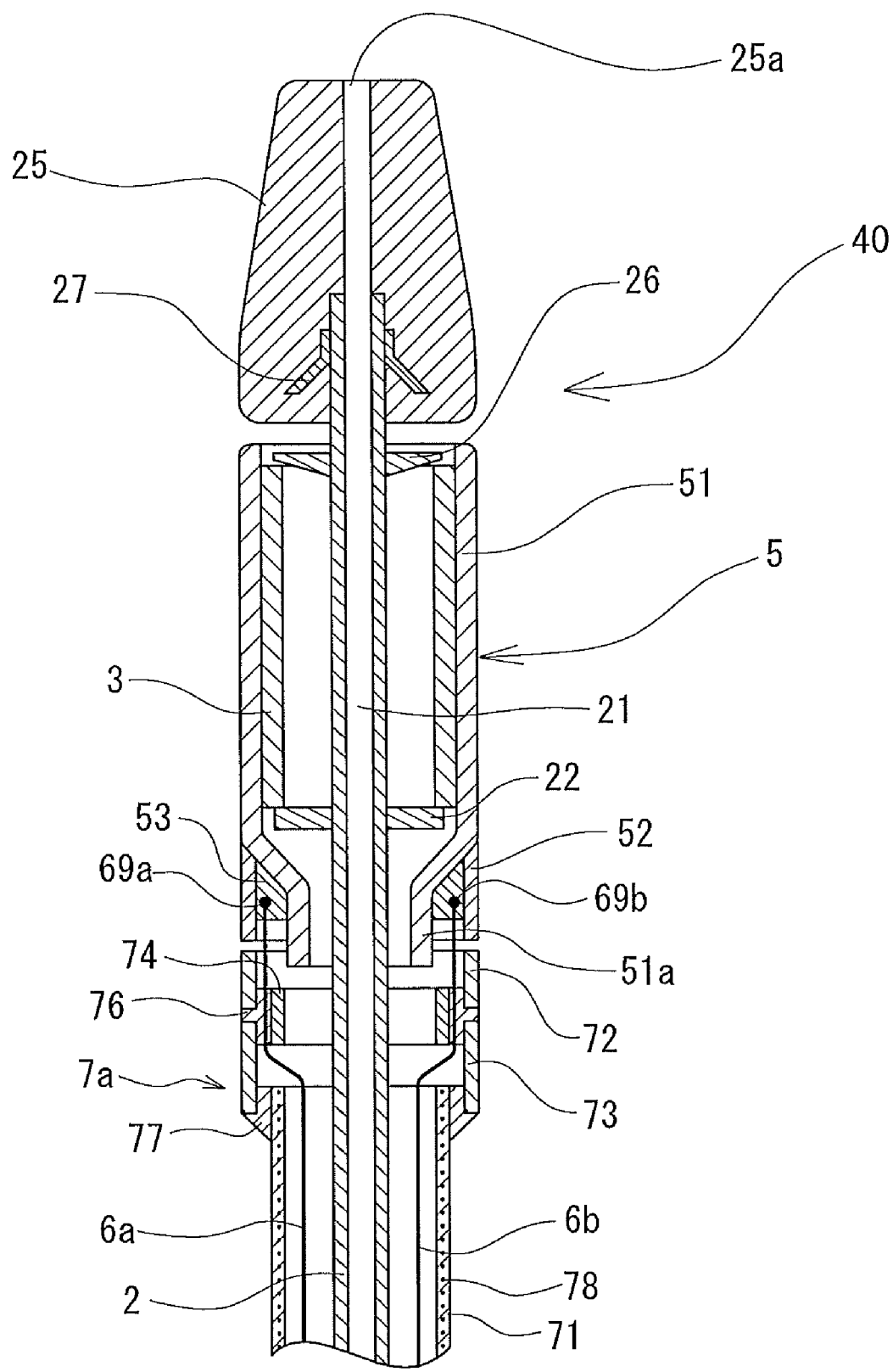
FIG. 13 is an enlarged cross-sectional view of the distal portion of a stent delivery system according to another embodiment disclosed here.

The stent delivery systems of all of the above-described embodiments may have a construction similar to that of the stent delivery system 40 shown in FIG. 13. In this version of the stent delivery system 40, the pulling wires 6a, 6b are fixed to the inner surface of a slide tube 7a.

Unlike the slide tube of the stent delivery system 1 described above, the slide tube 7a of this embodiment does not include the ring-shaped member 75 accommodated inside the slide tube in an unfixed (movable) state. More specifically, as shown in FIG. 13, the slide tube 7a includes a slide tube body 71 and a distal-side member fixed to the distal end of the slide tube body 71 and possessing outer and inner diameters larger than those of the slide tube body 71. In this embodiment, the distal-side member of the slide tube 7a includes: an outer tubular portion constructed of a first tubular member 72 and a second tubular member 73 having outer and inner diameters almost equal to those of the first tubular member 72; an inner tubular portion constructed of a third tubular member 74 disposed inside the proximal portion of the first tubular member 72 and inside the distal portion of the second tubular member 73; and a fixing portion 76 fixing together the outer tube and the inner tube, in other words fixing the first tubular member 72, the second tubular member 73, and the third tubular member 74 together and to the fixing portion 76. The pulling wires 6a, 6b are fixed to the fixing portion 76 and pass through the fixing portion. The pulling wires 6a, 6b are thus directly fixed to the slide tube 7a. The fixing portion 76 constitutes means for connecting the wire 6 to the slide tube 7a in a manner that the slide tube 7a is moved in the proximal direction when a pulling force is applied to the pulling wire 6 in the proximal direction. In this embodiment, because the force of the pulling wires 6a, 6b at the time of pulling is distributed to the fixing points 69a, 69b and the portion where the pulling wires 6a, 6b are fixed to the slide tube 7a, it is possible to help securely inhibit or prevent a fixed state between the pulling wires 6a, 6b and the stent accommodation tubular member 5 at the fixing points 69a, 69b from being released.

Figure 14:
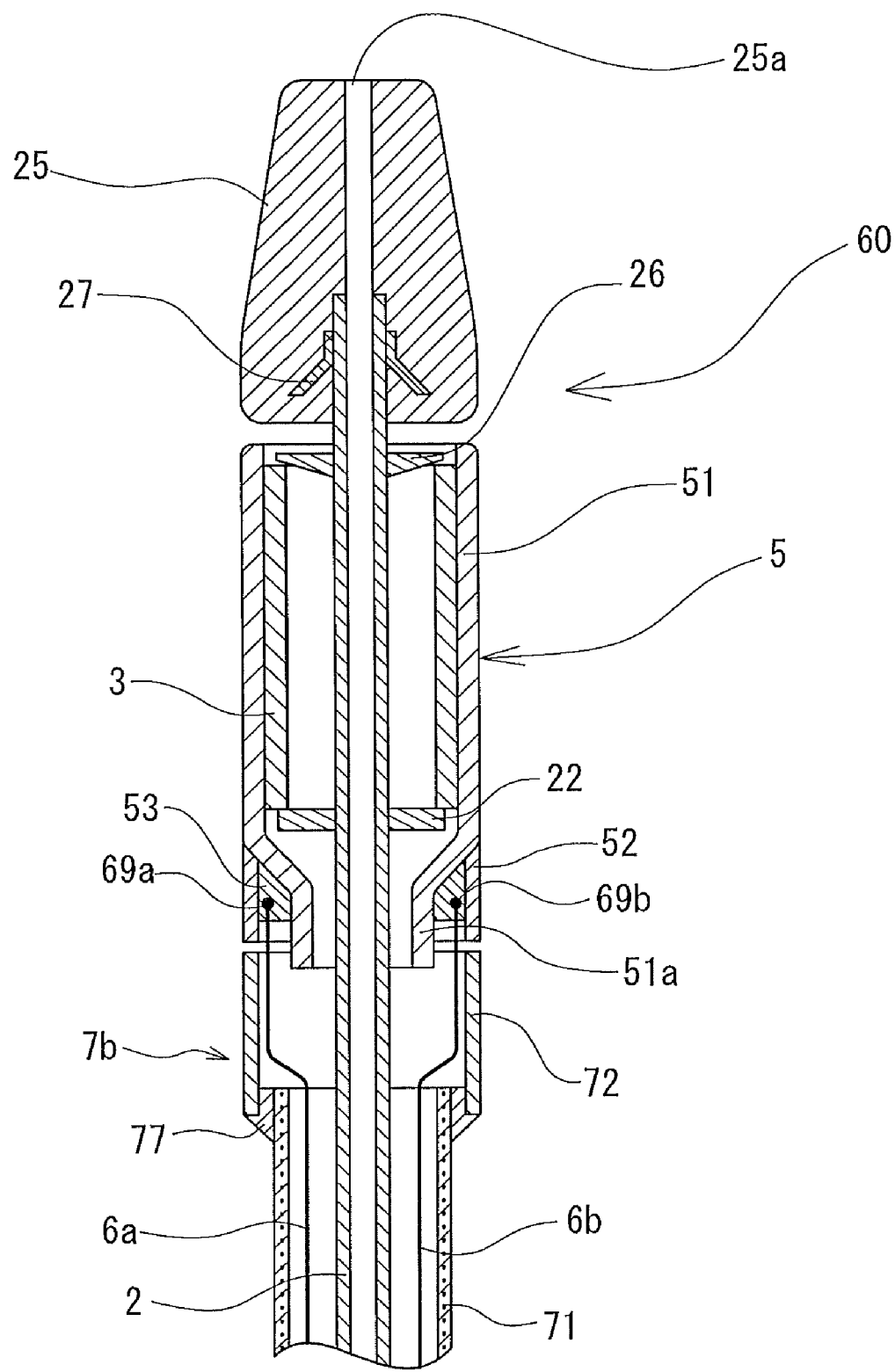
FIG. 14 is an enlarged cross-sectional view of the distal portion of a stent delivery system according to another disclosed embodiment.

All of the above-described embodiments of the stent delivery systems disclosed here may have a construction similar to that of a stent delivery system 60 shown in FIG. 14. In this stent delivery system 60, the pulling wires 6a, 6b are not fixed to the inner surface of the slide tube 7b. Unlike the stent delivery system 1, the stent delivery system 60 shown in FIG. 14 does not include the movable ring-shaped member 75 in the slide tube 7.

More specifically, as shown in FIG. 14, the slide tube 7b includes the slide tube body 71 and the distal-side member 72 which is fixed to the distal end of the slide tube body 71 and has outer and inner diameters larger than those of the slide tube body 71. The pulling wires 6a, 6b pass through the slide tube 7b without being fixed to the slide tube 7b.

Figure 15:
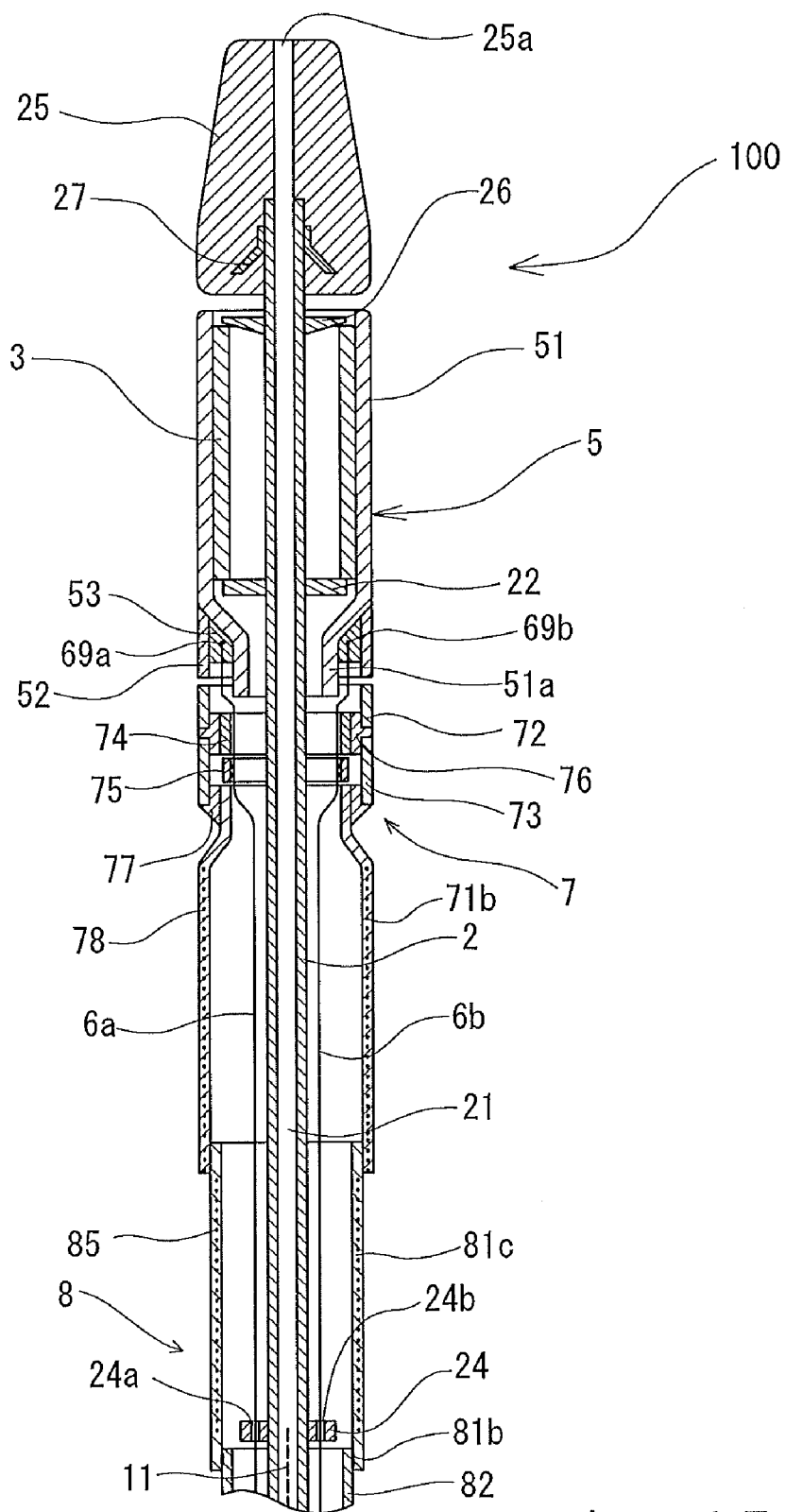
FIG. 15 is an enlarged cross-sectional view of the distal portion of a stent delivery system according to another embodiment disclosed here.

All of the above-described embodiments of the stent delivery systems may include a construction similar to that of a stent delivery system 100 shown in FIG. 15. The stent delivery systems described above include a fixing tube 8 of a type in which at the time of pulling the wire, the slide tube 7 is accommodated inside the fixing tube 8 from the proximal side of the slide tube 7. In other words, the fixing tube 8 is of a type in which the slide tube body 71b of the slide tube 7 penetrates into the fixing tube 8 from the proximal end of the slide tube 7.

On the other hand, the stent delivery system 100 of the embodiment shown in FIG. 15 is of a type in which at the time of pulling, the slide tube 7 encloses the fixing tube 8 from the proximal side of the slide tube 7. In other words, the fixing tube 8 here is configured so that the slide tube body 71b of the slide tube 7 receives and encloses the distal-side fixing tube 81c of the fixing tube 8 from the proximal end of the slide tube 7.

Therefore the inner diameter of the slide tube body 71b is almost equal to or a little larger than the outer diameter of the distal-side fixing tube 81c. The distal-side fixing tube 81c is fixed to the distal portion of the proximal-side fixing tube 82 at the proximal portion thereof by the fixing portion 81b. In this embodiment, the member 24 does not function as the slide tube-locking portion.

As shown in FIGS. 1 and 17-21, the stent delivery system 1 disclosed here includes the operation part 10 fixed to the proximal end of the proximal-side tube 4. FIGS. 17-21 illustrate various aspects and details associated with the operation part 10.

The operation part 10 of the stent delivery system 1 of this embodiment includes a pulling wire winding mechanism, a locking mechanism for releasably locking a rotation of the pulling wire winding mechanism, and a reverse rotation prevention mechanism for preventing the rotation of the pulling wire winding mechanism in a direction opposite to the direction in which the pulling wire is wound.

As shown in FIGS. 17-21, the operation part 10 includes an operation part housing 50 comprised of a first housing 50*a* and a second housing 50*b*. The operation part housing 50 is curved and rounded at its proximal side and central portion. Thus the operation part housing 50 can be relatively easily gripped and allows a roller to be easily operated in a gripped state.

Figure 19:
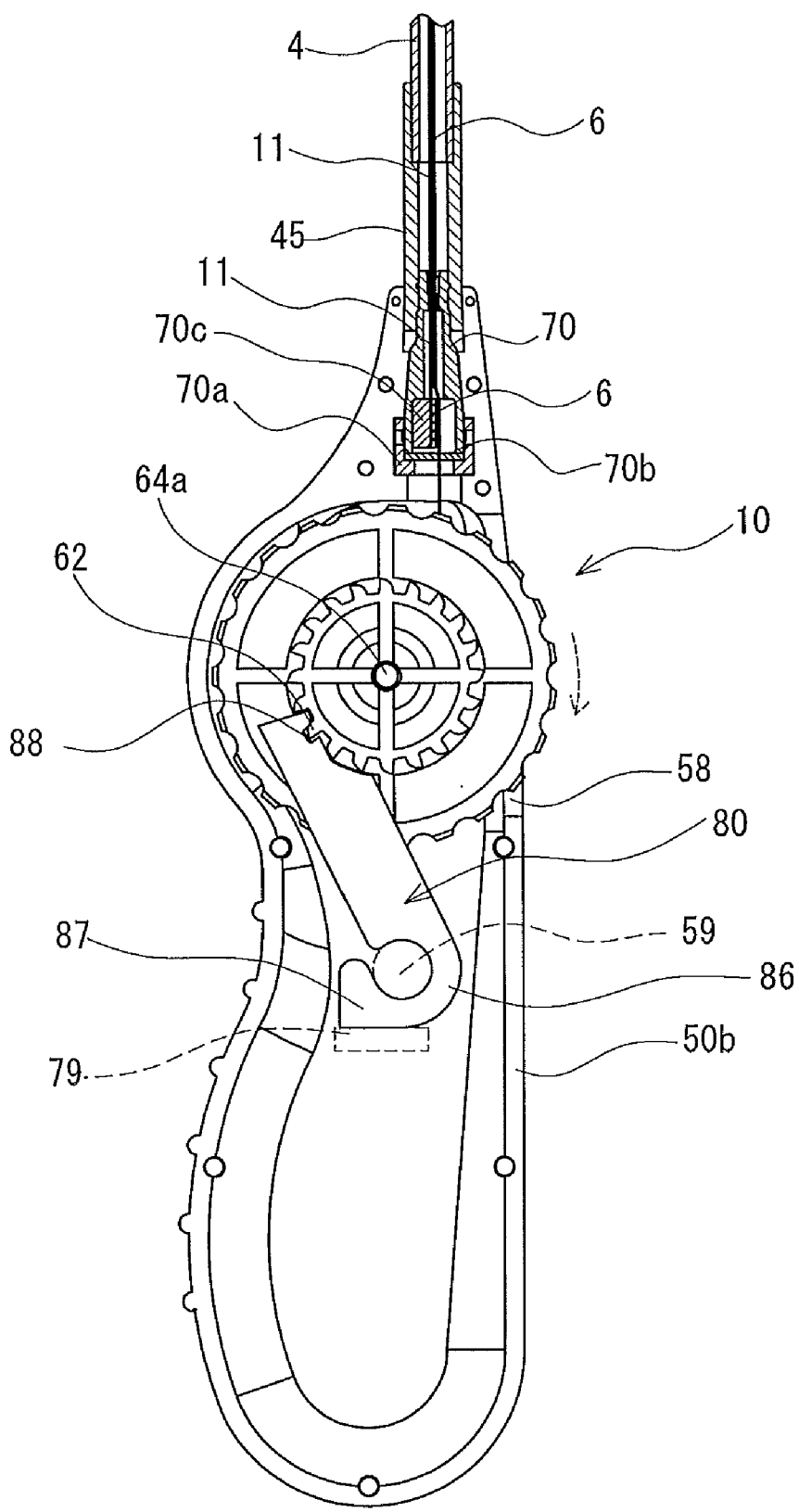
FIG. 19 is a partial cross-sectional view showing an inner construction of the operation part of the stent delivery system shown in FIG. 17.

As shown in FIG. 19, the distal portion of a tubular connector 45 is fixed to the proximal end of the proximal-side tube 4. A sealing mechanism connected to the proximal portion of the connector 45 is accommodated inside the operation part housing 50. As shown in FIG. 19, the sealing mechanism includes: a sealing mechanism tubular body member 70 having a distal portion fixed to the rear-end portion of the connector 45; a cap member 70*a* fixed to the proximal end of the tubular body member 70 and positioned in a hole in the distal end of the housing 50; a sealing member 70*b* disposed between the tubular body member 70 and the cap member 70*a*; and a rigidity-imparting member-fixing member 70*c* accommodated inside the tubular body member 70. The body member 70 and the cap member 70*a* have an open portion through which the pulling wire is penetrated or extends. The sealing member 70*b* has an open portion or a slit through which the pulling wire 6 (6*a*, 6*b*) extends in a liquid-tight and slidable manner. The proximal portion of the rigidity-imparting member 11 is fixed to the rigidity-imparting member-fixing member 70*c*. The rigidity-imparting member-fixing member 70*c* is fixed to the inside of the tubular body member 70. Materials for composing the sealing member are preferably elastic materials. Materials which can be used to fabricate the sealing member 70*b* include elastic materials.

Figure 17:
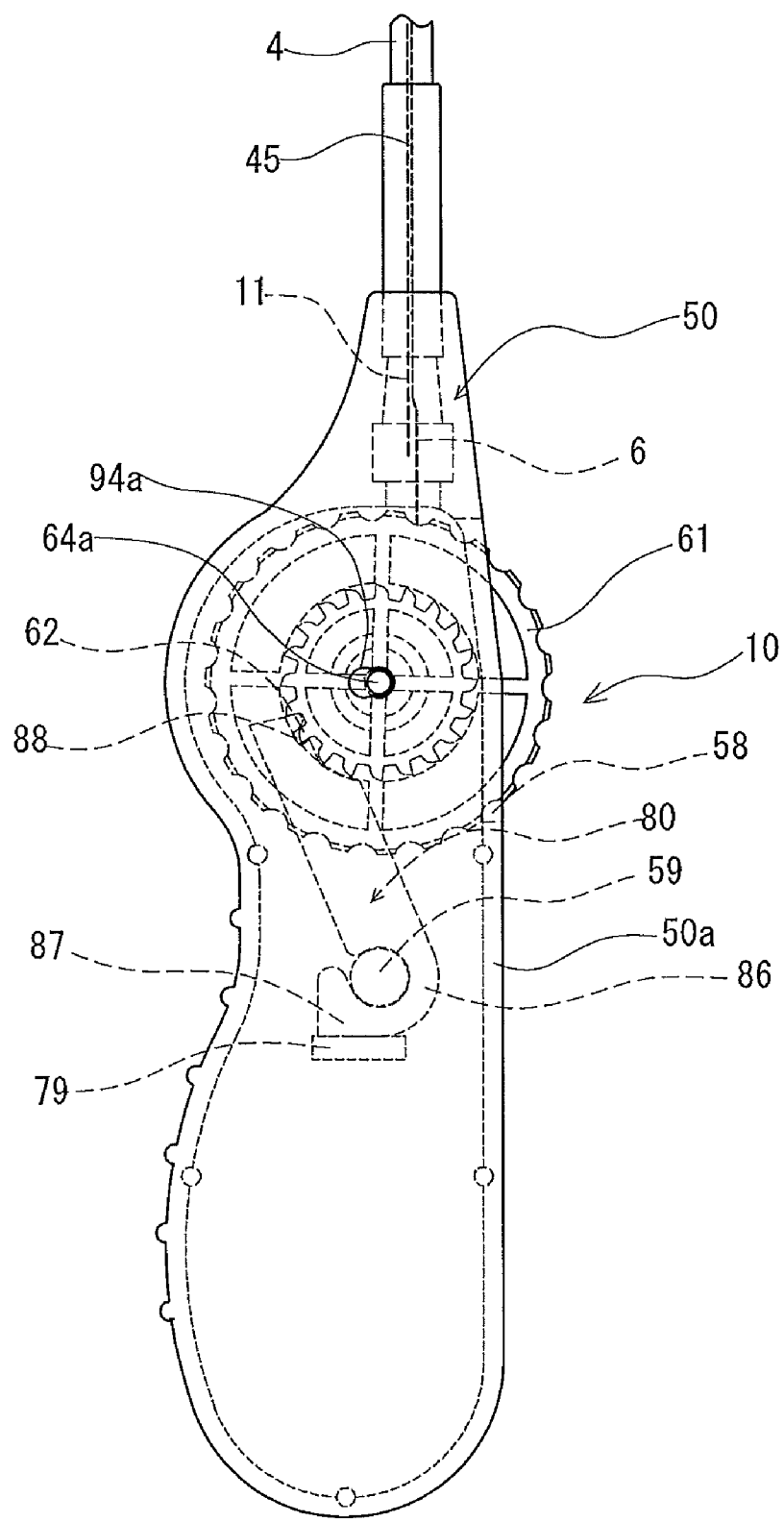
FIG. 17 is an enlarged front view of the neighborhood of the operation part of the stent delivery system disclosed here.
Figure 18:
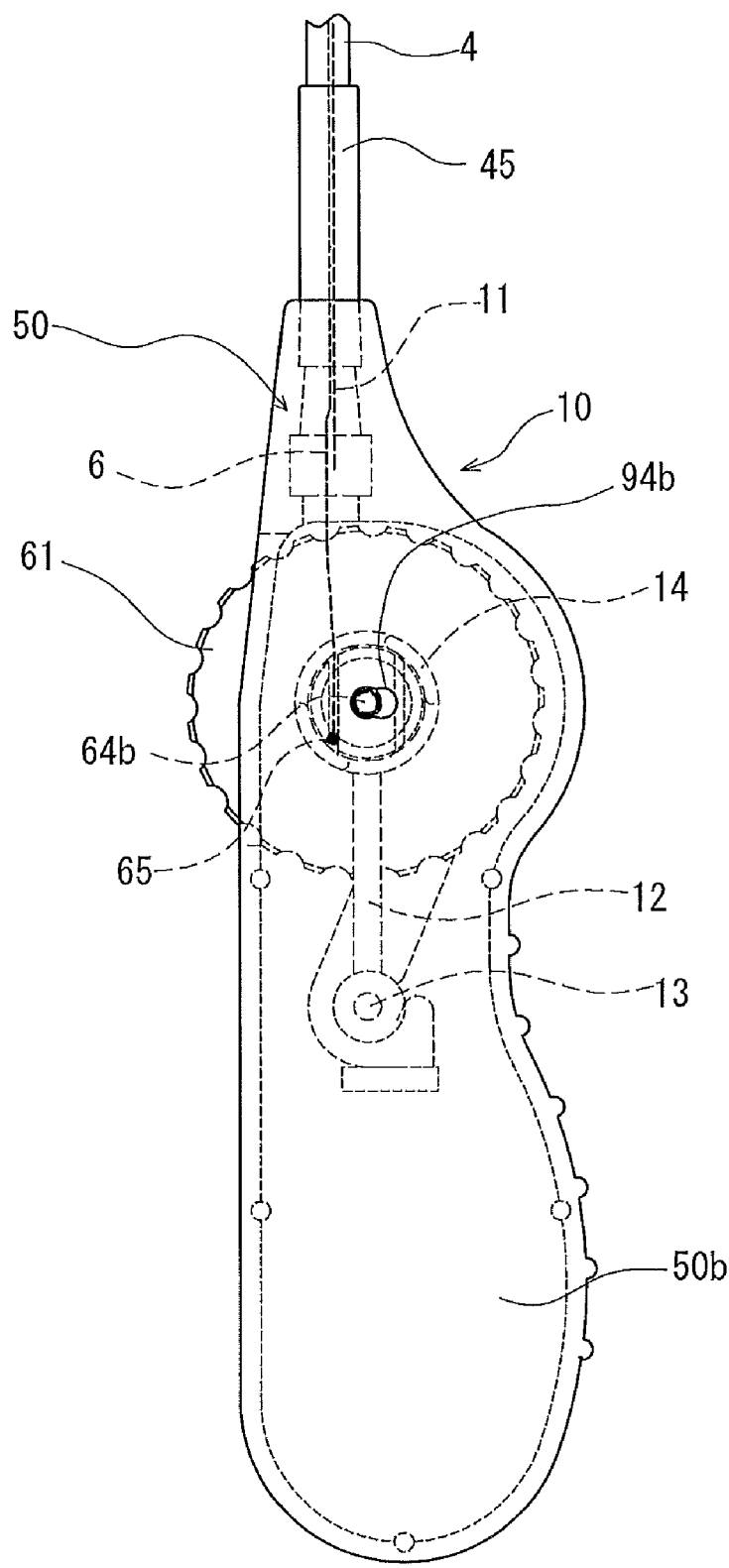
FIG. 18 is an enlarged rear view in the neighborhood of the operation part of the stent delivery system shown in FIG. 17.

As shown in FIGS. 17-20, the housing 50 includes an open portion 58 allowing a rotational roller 61 to partially project out of the housing for operational use, a locking rib (not shown) which engages a projection of a gear portion 62 provided on the roller 61, a bearing portion 94*b* accommodating one end 64*b* of a rotating shaft of the roller 61, and a bearing portion 94*a* accommodating the other end 64*a* of the rotating shaft of the roller 61. The locking rib is configured to penetrate between projections formed on the gear portion 62 of the roller 61. As shown in FIGS. 17 and 18, the bearing portions 94*a*, 94*b* accommodate the one end 64*b* and the other end 64*a* of the rotating shaft of the roller 61, are gourd-shaped and extend in a direction away from the open portion or opening 58. The configuration of the bearing portions 94*a*, 94*b* is not limited to that of a gourd, but may be so shaped that the bearing portions 94*a*, 94*b* are capable of moving a distance in which they can be disengaged from the locking rib. For example, the configuration of the bearing portions 94*a*, 94*b* may be oblong, rectangular or elliptical. As shown in FIGS. 17 and 18, in the operation part 10 of this embodiment, the bearing portions 94*a*, 94*b* are gourd-shaped. Therefore the rotational roller 61 for operational use is pressed to allow the ends 64*b*, 64*a* of the rotating shaft of the roller 61 accommodated in a space formed at one side of the bearing portions 94*a*, 94*b* to ride across opposed rib portions formed on the inner side surface of the central portion of the bearing portions 94*a*, 94*b*. Thereby the ends 64*b*, 64*a* of the rotating shaft of the roller 61 are accommodated in a space formed at the other side of the bearing portions 94*a*, 94*b*. FIG. 19 shows a state in which the roller 61 is pressed. In this state, the roller 61 is pressed by an urging member. Thereby the ends 64*b*, 64*a* of the rotating shaft of the roller 61 contact the opposed ribs formed on the inner side surface of the central portion of the bearing portions 94*a*, 94*b* and thus do not move to the space formed at the one side of the bearing portions 94*a*, 94*b*. Therefore the roller 61 maintains a rotatable state.

Figure 21:
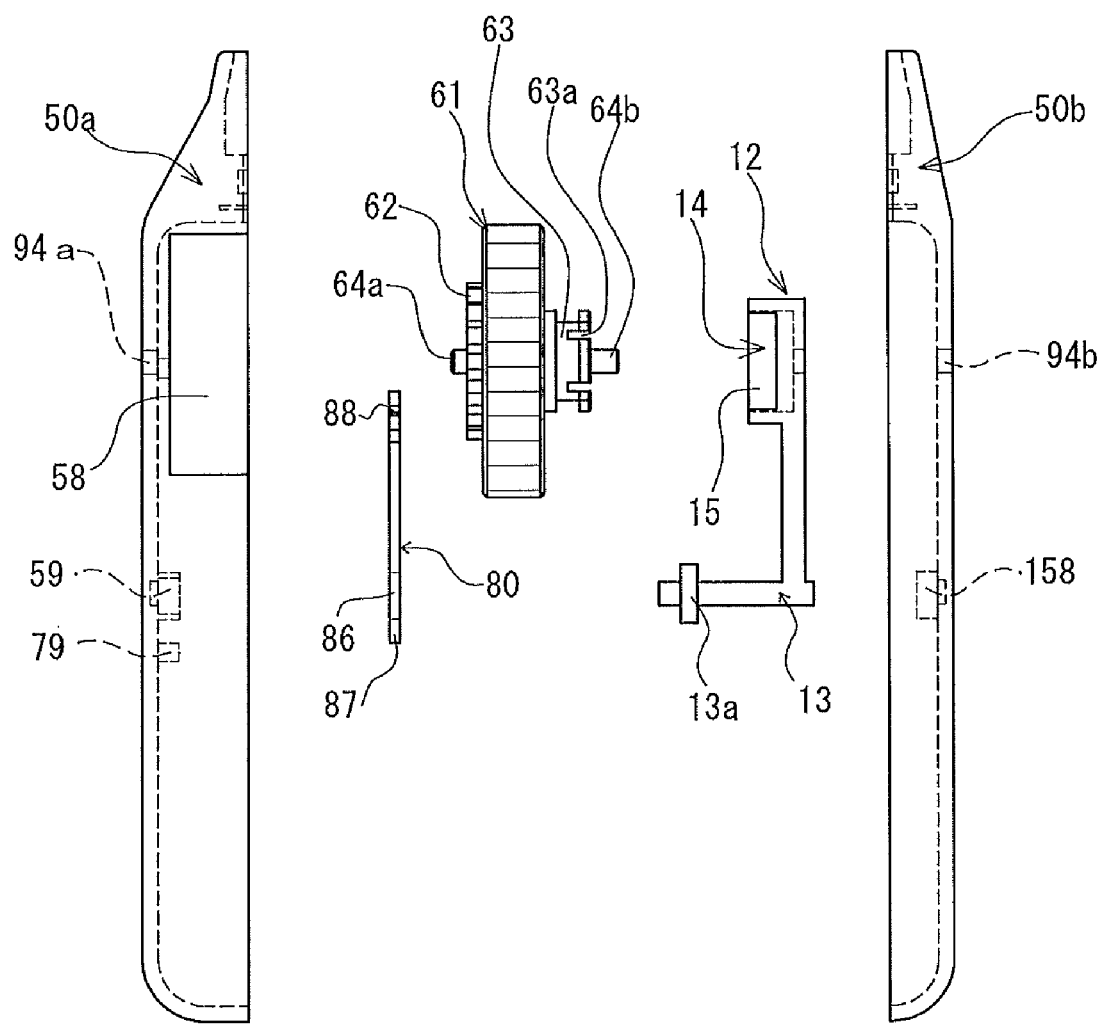
FIG. 21 is an exploded view illustrating the inner construction of the operation part of the stent delivery system shown in FIG. 17.

As shown in FIGS. 18 and 21, in this embodiment, the operation part 10 has a collar member 12. The collar member 12 includes a collar portion 14 accommodating a winding shaft portion 63 and forming an annular space between it and the winding shaft portion 63. The collar portion 14 prevents the pulling wire wound around the winding shaft portion 63 from becoming loose. The collar member 12 functions to guiding the rotational roller in its movement when the rotational roller is pressed and to restraining backlash of the rotational roller. A pin 13 of the collar member 12 is supported by a projection (bearing portion) 59 of the first housing 50*a* and a concavity (bearing portion) 158 of the second housing 50*b*. As shown in FIGS. 17 and 18, the bearing portions 94*a*, 94*b* are formed in the shape of a gentle circular arc about the pin 13. The bearing portions 94*a*, 94*b* have a length allowing the roller 61 to move a distance longer than the height of the locking rib. As shown in FIG. 21, the collar member 12 has two cut-out portions 15 which reach a space inside a collar portion 14 from the side surface thereof. The pulling wire 6 penetrates through one of the cut-out portions 15 and is fixed to the winding shaft portion 63.

The pulling wire winding mechanism is constructed of the roller 61 and the winding shaft portion 63 which is rotated by the rotation of the roller 61. The proximal portion of the pulling wire 6 is held by the winding shaft portion 63 or secured thereto. More specifically, as shown in FIG. 18, an anchoring portion 65 formed larger than the wire 6 is provided at the proximal portion of the pulling wire 6. A slit 63*a* capable of accommodating the pulling wire 6 is formed at the winding shaft portion 63. The slit 63*a* of the winding shaft portion 63 accommodates the proximal portion of the pulling wire 6, with the anchoring portion 65 disposed outward from the slit 63*a*. Thereby when the winding shaft portion 63 rotates, the wire 6 is wound on the outer surface of winding shaft portion 63. The method of holding the proximal portion of the pulling wire 6 on the winding shaft portion 63 or securing the pulling wire 6 to the winding shaft portion 63 is not limited to the above-described method, as any methods can be used. For example, the proximal end of the pulling wire 6 or the proximal portion of the pulling wire may be directly secured to the winding shaft.

It is preferable, so that the proximal portion of the pulling wire 6 can be wound on the winding shaft portion 63, that the proximal portion of the pulling wire is relatively flexible to allow the pulling wire 6 to be wound relatively easily. To make the proximal portion of the pulling wire 6 relatively flexible, the proximal portion of the pulling wire 6 can be made of a flexible material and/or the diameter of the proximal portion of the pulling wire 6 can be decreased.

Figure 20:
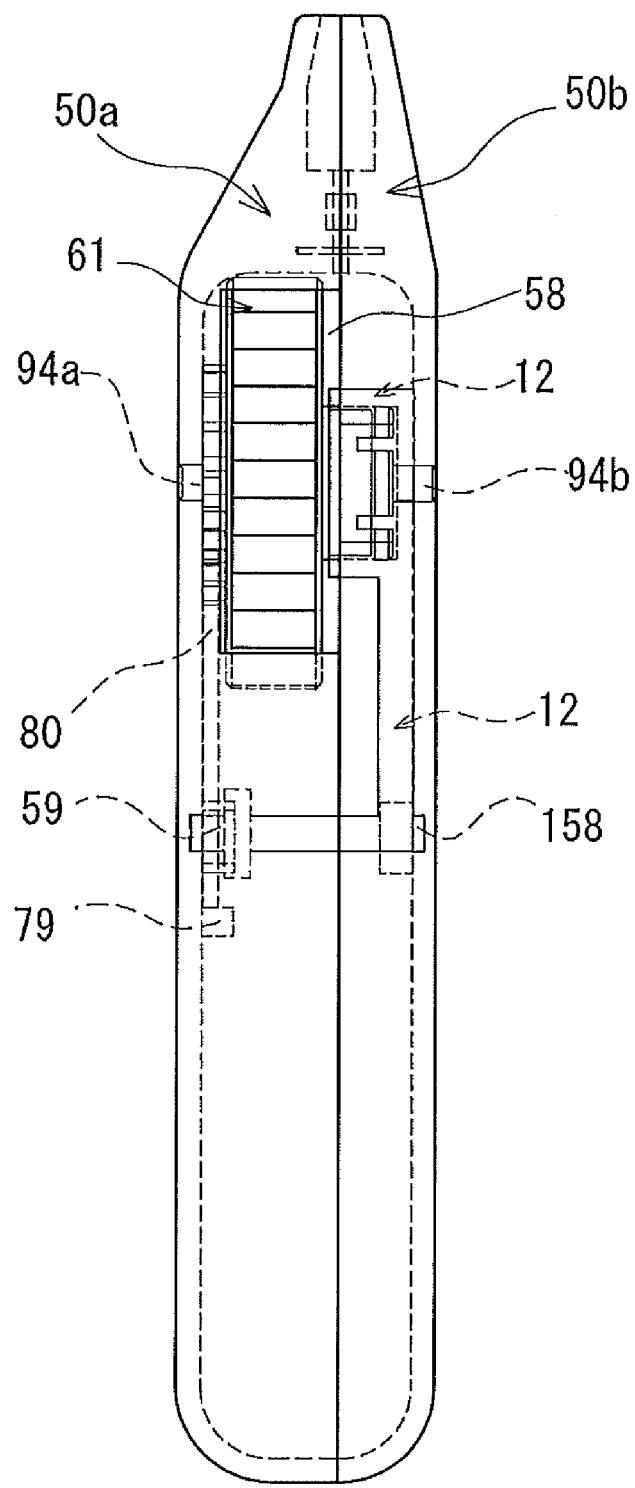
FIG. 20 is a right-hand side elevational view of only the operation part of the stent delivery system shown in FIG. 17.

In this embodiment, the winding shaft portion 63 is integral with the rotational roller 61 to make the winding shaft portion 63 and the rotational roller 61 coaxial with each other and unitary in construction. As shown in FIGS. 17, 19 and 20, the winding shaft portion 63 is provided on, or axially projects from, one side surface of the rotational roller 61. By rotating the rotational roller 61, the winding shaft portion 63 rotates simultaneously with the rotational roller 61. It is preferable that the winding amount of the pulling wire is smaller than that of an operation required to rotate the rotational roller. By doing so, the pulling wire can be wound slowly. Moreover, the stent accommodation tubular member is allowed to move toward the proximal side slowly and favorably. In this embodiment, because the outer diameter of the winding shaft portion is smaller than that of the rotational roller for operational use, the winding amount of the pulling wire is smaller than that of the operation of rotating the rotational roller.

The outer diameter of the winding shaft portion 63 is preferably 1 to 60 mm, preferably 3 to 30 mm. The outer diameter of the rotational roller is preferably 1 to 20 times, preferably 1 to 10 times larger than that of the winding shaft portion. The outer diameter of the rotational roller is preferably 10 to 60 mm, preferably 15 to 50 mm.

The rotational roller and the winding shaft portion do not necessarily have to be formed integrally. The winding shaft portion may be constructed of a separate member which follows the rotation of the rotational roller. As the transmission system of the rotational roller, it is possible to use a gear type, a belt type, or the like. It is preferable that surfaces of parts which have a possibility of contacting the surface of the rotational roller 61 while operating the rotational roller 61 are not slippery. For example, it is preferable to treat surfaces of parts which have a possibility of contacting the surface of the rotational roller 61 during operation of the rotational roller 61 by knurling treatment, emboss treatment, application of a high-frictional material, and the like.

The operation part 10 of this embodiment includes a locking mechanism for releasably locking the rotation of the pulling wire winding mechanism, and a reverse rotation prevention mechanism for preventing the rotation of the pulling wire winding mechanism in the direction opposite to the direction in which the pulling wire is wound.

As shown in FIGS. 17-19, the rotational roller 61 includes a gear portion 62 which is coaxial with the rotational roller 61 and rotates together with the rotational roller 61. As shown in FIGS. 18 and 20, the gear portion 62 is provided on the other side surface of the rotational roller 61. In other words, the gear portion 62 is on a surface on the opposite axial side of the roller 61 from the winding shaft portion 63. Thus the gear portion 62 and the winding shaft portion 63 are partitioned or separated from each other by a wall constituted by the manually operable roller portion.

The rotational roller 61 for operational use is partly exposed from the open portion 58. The exposed portion serves as the operation part that is manually operated or rotated by the user. The rotational roller includes the other end 64a of the rotational shaft provided on one side surface (more specifically, side surface of gear portion) of the rotational roller and the one end 64b of the rotational shaft provided on the other side surface (more specifically, side surface of winding shaft) of the rotational roller.

An urging means (urging member) 80 for urging the rotational roller 61 is provided inside the housing 50. More specifically, the urging means 80 urges the roller 61 toward the open portion 58 of the housing. The housing 50 accommodates the locking rib (not shown) capable of penetrating into the gap between adjacent projections formed on the gear portion 62 of the roller 61. Therefore when the rotating roller 61 is urged by the urging member 80, the rotating roller 61 is in the state shown in FIG. 18. Because the locking rib engages the projection of the gear portion 62, the rotating roller 61 is incapable of rotating. When the rotating roller 61 is pressed in the direction in which it moves away from the locking rib, the one end 64b and other end 64a of the rotating shaft of the rotating roller 61 move inside the bearing portions 94b, 94a respectively provided in the housing 50, and thus the rotational roller 61 becomes rotatable. Therefore the operation part 10 of this embodiment prevents the rotation of the rotational roller 61 when it is not pressed and has the locking mechanism for releasably locking the rotation of the pulling wire winding mechanism.

In the operation part of this embodiment, the urging means 80 and the gear portion 62 constitute the reverse rotation prevention mechanism for preventing the rotational roller from rotating in the direction opposite to the direction in which the pulling wire of the pulling wire winding function is wound (i.e., for preventing the rotational roller from rotating in the direction in which the pulling wire of the pulling wire winding function is unwound).

As shown in FIGS. 17-20, the rotational roller 61 includes the gear portion 62 which is coaxial with the rotational roller 61 and rotates together with the rotational roller 61. As shown in FIG. 20 and mentioned above, the gear portion 62 is disposed on a surface of the roller 61 opposite to the surface on which the winding shaft portion 63 of the rotational roller 61 is disposed. Thus the gear portion 62 and the winding shaft portion 63 are separated from each other by a wall constructed of the rotational roller for operational use.

As shown in FIGS. 17-19, the reverse rotation prevention mechanism is provided inside the operation part 10. The operation part 10 has the reverse rotation prevention mechanism provided on the urging member 80. More specifically, the urging member 80 serves as the reverse rotation prevention member. The reverse rotation prevention mechanism includes: an engaging portion 88, disposed at a portion opposed to the gear portion 62 of the rotational roller 61, capable of engaging the gear portion; an elastically deformable portion 86; and a portion 87 to be mounted on the housing. The first housing 50a has a first projection (bearing portion) 59 and a second projection 79, both formed on the inner surface of the first housing 50a. The first projection 59 penetrates into the elastically deformable portion 86 of the reverse rotation prevention member (urging member) 80 and has an outer configuration corresponding to the inner configuration of the elastically deformable portion 86. More specifically, the inner surface of the elastically deformable portion 86 is circular arc-shaped. The first projection 59 is tubular in correspondence with the circular arc configuration. The portion 87 to be mounted on the housing of the reverse rotation prevention member (urging member) 80 is so configured as to be mounted between the first projection 59 and the second projection 79 formed on the first housing 50a. Because the portion 87, to be mounted on the housing, of the reverse rotation prevention member (urging member) 80 is mounted between the first projection 59 and the second projection 79, the reverse rotation prevention member 80 is incapable of rotating and urges the operational rotational roller 61 toward the open portion 58 by the elastic force of the elastically deformable portion 86. A disk-shaped projection 13a of the collar member 12 prevents the portion 87 mounted on the housing of the reverse rotation prevention member (urging means) 80 from moving toward the side surface thereof.

As described above, by pressing the roller 61, the roller can be rotated. The roller 61 is rotatable in the direction (pulling wire-winding direction) shown with the arrow of FIG. 19. But if an operation of rotating the roller 61 in the opposite direction is performed, one cog of the gear portion 62 and the engaging portion 88 of the reverse rotation prevention mechanism (urging member) 80 engage each other. Thus the rotation of the roller 61 is prevented. Thereby the reverse rotation prevention function prevents the roller of the pulling wire winding mechanism from rotating in the direction opposite to the pulling wire winding direction. As shown in FIG. 20, in the operation part 10, the reverse rotation prevention member (urging member) 80 is disposed between the inner surface of the first housing 50a and the side surface of the rotational roller 61. Therefore the movement of the reverse rotation prevention member (urging member) 80 in a lateral direction (horizontal direction) is prevented by the inner surface of the first housing 50a and the side surface of the rotational roller 61.

The diameter of the gear portion 62 is smaller than that of the rotational roller. The outer diameter of the gear portion 62 is preferably 10 to 60 mm, preferably 15 to 50 mm. The number of cogs is preferably 4 to 200, preferably in the range of 4 to 70.

The collar member 12 of the operation part 10 is supported with the pin 13 at its one end. The collar portion 14 at the other side of the collar member 12 accommodates the winding shaft portion 63 and forms an annular space between the collar portion 14 and the winding shaft portion 63. The annular space is not very large and forms a relatively small annular space between the collar portion and the outer surface of the wound wire.

The method of using the stent delivery system 1 disclosed here is described below with reference to the drawings.

As shown in FIGS. 1 and 2, one end of the guide wire already indwelled in an organism is inserted into the open end 25a of the distal-end member of the stent delivery system and is fed along the stent delivery system so that the guide wire extends out from the opening 23. Thereafter the guide wire is inserted into a guiding catheter (not shown) inserted into the organism. Thereafter the stent delivery system 1 is moved forward along the guide wire to position the stent accommodation portion of the stent accommodation tubular member 5 inside a desired stenosed portion.

After the rotational roller 61 for operational use of the operation part 10 is pressed, the roller is rotated in the direction shown with the arrow in FIG. 19. Thereby the pulling wire 6 is wound around the peripheral surface of the winding shaft 63, and the stent accommodation tubular member 5 and the slide tube 7 move axially in the proximal direction to the axial proximal side. At this time, the rear end surface of the stent 3 contacts the distal surface of the stent-locking portion 22 of the distal-side tube 2 and remains thereto. At this time, as the stent accommodation tubular member 5 moves, the stent 3 is discharged from the opening disposed at the distal end of the stent accommodation tubular member 5. As shown in FIG. 10, owing to the discharge, the stent 3 self-expands, expands the stenosed portion, and is implanted in the stenosed portion.

In the embodiments of the stent delivery system disclosed here, even though the twisted force imparted at the proximal portion of the system is transmitted to the slide tube, the twisted force is transmitted to the stent accommodation tubular member to a very low extent. Therefore the twist force is imparted to the stent accommodated inside the stent accommodation tubular member to a very low extent. Further in the stent delivery system described by way of the embodiments here, when the pulling wire is pulled, the stent accommodation tubular member is deformed to a relatively low extent. Thus the stent accommodation tubular member can be moved favorably toward the proximal end, and the outer tube for discharging the stent can be relatively easily moved. Therefore the stent-implanting operation can be performed relatively easily and securely.

The stent delivery system disclosed here uses a self-expandable stent, allows relatively easy movement of the outer tube for discharging the stent, permits a stent-implanting operation to be performed relatively easily and securely, and helps restrain twist force imparted at a proximal portion from being transmitted to the stent accommodation tubular member while inserting the stent into an organism so that the twist force is imparted to the stent accommodated inside the stent accommodation tubular member to a very low extent.

The principles, embodiments and modes of operation of the stent delivery system have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. A stent delivery system comprising:
   a distal-side tube possessing a guide wire lumen through which a guide wire is adapted to extend;
   a proximal-side tube having an interior;
   a fixing tube fixed to a proximal portion of the distal-side tube and a distal portion of the proximal-side tube, the fixing tube possessing an opening communicating with the guide wire lumen;
   a stent accommodation tubular member enclosing a distal side of the distal-side tube and slidable toward a proximal end of the distal-side tube, the stent accommodation tubular member possessing a proximal end;
   a cylindrically-shaped stent accommodated inside the stent accommodation tubular member in a compressed condition and being expandable outwardly when the stent is discharged from the stent accommodation tubular member so the stent returns to a configuration exhibited by the stent before being accommodated in the stent accommodation tubular member in the compressed condition;
   at least one pulling wire possessing one end portion fixed relative to the stent accommodation tubular member so that movement of the one end portion of the wire toward a proximal side of the stent accommodation tubular member causes movement of the stent accommodation tubular member toward the proximal side;
   the distal-side tube comprising a stent proximal portion-locking portion which contacts a proximal end of the stent accommodated inside the stent accommodation tubular member to prevent the stent from moving toward the proximal side;
   a slide tube disposed proximally of the proximal end of the stent accommodation tubular member, the slide tube not being fixed to the stent accommodation tubular member;
   the slide tube being movable toward the proximal side, together with the stent accommodation tubular member, when the pulling wire is pulled toward the proximal side so the slide tube either is received inside the fixing tube or receives the fixing tube.

2. A stent delivery system according to claim 1, wherein the pulling wire is fixed at a fixing region to an inner surface of the slide tube or is fixed at the fixing region to a member which is moved by being pulled by pulling wire, the fixing region being positioned on the proximal side of the one end portion of the pulling wire that is fixed relative to the stent accommodation tubular member.

3. A stent delivery system according to claim 1, further comprising a ring-shaped member accommodated inside the slide tube and movable together with the slide tube, the pulling wire being fixed to the ring-shaped member so that pulling of the pulling wire toward the proximal side causes the ring-shaped member to move toward the proximal side.

4. A stent delivery system according to claim 3, wherein the slide tube comprises a ring-shaped member-holding portion accommodated inside the slide tube in an unfixed state, the ring-shaped member-holding portion holding the ring-shaped member in a manner allowing the ring-shaped member to freely rotate in the ring-shaped member-holding portion while substantially preventing the ring-shaped member from axially moving relative to the ring-shaped member-holding portion.

5. A stent delivery system according to claim 1, wherein a proximal end of the slide tube is positioned in the fixing tube and the slide tube is slidably movable inside the fixing tube as the pulling wire is pulled toward the proximal side, and a slide tube-locking portion is fixed to the distal-side tube, the slide tube-locking portion being positioned inside the fixing tube and being contacted by a proximal end of the slide tube as the pulling wire is pulled toward the proximal side.

6. A stent delivery system according to claim 5, further comprising a linear rigidity-imparting member extending inside the proximal-side tube and extending inside the fixing tube, the rigidity-imparting member possessing a distal portion fixed to the slide tube-locking portion.

7. A stent delivery system according to claim 6, wherein the fixing tube comprises a rigidity-imparting member-fixing portion disposed nearer to a proximal end of the stent delivery system than the slide tube-locking portion.

8. A stent delivery system according to claim 1, wherein the stent accommodation tubular member comprises a smaller-diameter portion at a proximal portion of the stent accommodation tubular member, the smaller-diameter portion possessing an outside diameter smaller than the outside diameter of a distally located portion of the stent accommodation tubular member, the slide tube enclosing a proximal portion of the smaller-diameter portion of the stent accommodation tubular member.

9. A stent delivery system according to claim 1, wherein the stent accommodation tubular member comprises a smaller-diameter portion at a proximal portion of the stent accommodation tubular member, the smaller-diameter portion possessing an outside diameter smaller than the outside diameter of a distally located portion of the stent accommodation tubular member, a distal portion of the pulling wire being fixed to an outer surface of the smaller-diameter portion of the stent accommodation tubular member.

10. A stent delivery system according to claim 1, wherein the stent accommodation tubular member comprises a smaller-diameter portion at a proximal portion of the stent accommodation tubular member, the smaller-diameter portion possessing an outside diameter smaller than the outside diameter of a distally located portion of the stent accommodation tubular member, a distal portion of the pulling wire being fixed by a ring-shaped member fixed to the outer surface of the smaller-diameter portion.

11. A stent delivery system according to claim 1, wherein the stent accommodation tubular member comprises a smaller-diameter portion at a proximal portion of the stent accommodation tubular member, the smaller-diameter portion possessing an outside diameter smaller than the outside diameter of a distally located portion of the stent accommodation tubular member, and a tubular portion enclosing the smaller-diameter portion.

12. A stent delivery system according to claim 1, further comprising an operation part connected to a proximal portion of the proximal-side tube, the operation part comprising a rotatable pulling wire winding mechanism to which a proximal end of the pulling wire is connected, the pulling wire winding mechanism being rotatable to wind the pulling wire and move the stent accommodation tubular member toward the proximal side.

13. A stent delivery system according to claim 12, wherein the operation part comprises a housing, and the pulling wire winding mechanism comprises a rotatable roller, a portion of the rotatable roller being exposed outside the housing to be manually rotated to wind the pulling wire.

14. A stent delivery system according to claim 12, the operation part comprising a locking mechanism for releasably locking rotation of the rotating roller of the pulling wire winding mechanism.

15. A stent delivery system according to claim 12, wherein the operation part comprises a reverse rotation prevention mechanism which prevents the rotating roller of the pulling wire winding mechanism from rotating in a direction opposite to a pulling wire winding direction in which the pulling wire is wound.

16. A stent delivery system according to any one of claim 12, wherein the pulling wire winding mechanism comprises a rotatable roller and a winding shaft portion, the winding shaft portion possessing an outside diameter smaller than the outside diameter of the rotational roller, the winding shaft portion being coaxial with and of a unitary one-piece construction with the rotational roller, and a proximal portion of the pulling wire is fixed to the winding shaft portion.

17. A stent delivery system comprising:
a distal-side tube in which extends a guide wire lumen adapted to receive a guide wire to direct the stent delivery system to a desired site, the guide wire lumen extending from a distal end of the distal-side tube to a proximal end of the distal-side tube;
a proximal-side tube at least partially axially overlapping the distal-side tube, the proximal-side tube possessing an interior;
a fixing tube having a proximal portion fixed to the distal-side tube, the fixing tube possessing an opening communicating with the guide wire lumen;
a stent accommodation tubular member surrounding a portion of the distal-side tube and possessing a proximal-most end located distally of a distal-most end of the proximal-side tube, the stent accommodation tubular member surrounding a space;
a stent positioned in the space in a compressed condition and expandable outwardly when the stent is discharged from the space in the stent accommodation tubular member;
a pulling wire;
connecting means for connecting the pulling wire and the stent accommodation tubular member so that the stent accommodation tubular member is moved in the proximal direction when a pulling force in the proximal direction is applied to the pulling wire;
a slide tube positioned axially between the stent accommodation tubular member and the fixing tube, the slide tube not being fixed to the stent accommodation tubular member, the slide tube being axially movable together with the stent accommodation tubular member and being axially movable relative to the fixing tube;
the slide tube moving in the proximal direction relative to the fixing tube when the pulling wire is pulled in the proximal direction to cause axial overlap between the slide tube and the fixing tube that increases with continued movement of the slide tube in the proximal direction relative to the fixing tube.

18. A stent delivery system according to claim 17, wherein the pulling wire is fixed to an inner surface of the slide tube so that pulling the pulling wire in the proximal direction causes the slide tube to move in the proximal direction.

19. A stent delivery system according to claim 17, further comprising a ring-shaped member accommodated inside the slide tube and movable together with the slide tube, the pulling wire being fixed to the ring-shaped member so that the pulling force applied to the pulling wire in the proximal direction moves the slide tube in the proximal direction by virtue of the pulling wire being fixed to the ring-shaped member.

20. A stent delivery system according to claim 1, further comprising a ring-shaped member positioned in a ring-shaped member-holding portion in the slide tube in a manner allowing the ring-shaped member to rotate in the ring-shaped member-holding portion, the pulling wire being fixed to the ring-shaped member so that the pulling force applied to the pulling wire in the proximal direction moves the slide tube in the proximal direction by virtue of the pulling wire being fixed to the ring-shaped member.

* * * * *